United States Patent [19]

Lyons et al.

[11] Patent Number: 5,428,135
[45] Date of Patent: Jun. 27, 1995

[54] PRODUCTION OF PLATELET-DERIVED GROWTH FACTOR B-CHAIN HETERODIMERS FROM HIGH EXPRESSION HOST CELL SYSTEM

[75] Inventors: David E. Lyons; Arlen R. Thomason, both of Thousand Oaks, Calif.

[73] Assignee: Amgen Inc., Thousand Oaks, Calif.

[21] Appl. No.: 236,880

[22] Filed: Apr. 29, 1994

Related U.S. Application Data

[63] Continuation of Ser. No. 623,671, Dec. 12, 1990, abandoned, which is a continuation-in-part of Ser. No. 451,485, Dec. 15, 1989, abandoned.

[51] Int. Cl.⁶ .................... C12N 15/00; C12N 15/18; A61K 38/18
[52] U.S. Cl. .................... 530/399; 530/350; 435/69.1; 435/69.4
[58] Field of Search .......... 435/69.1, 69.4; 530/324, 350, 399; 514/12

[56] References Cited

U.S. PATENT DOCUMENTS

| | | | |
|---|---|---|---|
| 4,766,073 | 8/1988 | Murray et al. | 435/172.3 |
| 4,766,205 | 8/1988 | Ghosh-Dastidar | 530/402 |
| 4,769,328 | 9/1988 | Murray et al. | 435/68 |
| 4,845,075 | 7/1989 | Murray et al. | 514/12 |
| 4,889,919 | 12/1989 | Murray et al. | 530/351 |
| 5,045,633 | 9/1991 | Murray et al. | 530/399 |
| 5,128,321 | 7/1992 | Murray et al. | 514/12 |
| 5,149,792 | 9/1992 | Thomason | 530/399 |

FOREIGN PATENT DOCUMENTS

| | | |
|---|---|---|
| 9004035 | 4/1990 | WIPO. |
| 9008163 | 7/1990 | WIPO. |
| WO9108762 | 6/1991 | WIPO. |

OTHER PUBLICATIONS

Betscholtz et al., *Nature.* 320, 695–699 (1986).
Hoppe et al., *Biochemistry,* 28, 2956–2960 (1989).
Light, *Biotechniques,* 3(4), 298–306 (1985).
Devare et al., *Cell,* 36, 43–49 (1984).
Wang et al., *J. Biol. Chem.,* 259, 10645–10648 (1984).
Giese et al., *Science,* 236, 1315–1318 (1987).
Jaumann et al. *Biochemistry,* 30(13), 3303–3309 (1991).
Andersson et al., *J. Biol. Chem.,* 267(16), 11260–11266 (1992).
Stryer et al., *Biochemistry,* 2nd Edition, W. H. Freeman and Company, San Francisco, (1981), pp. 343–344.
Sauer et al., *Mol. Cell. Biol.,* 8(1), 1011–1018, (1988).
Maher et al., *Oncogene,* 8(3), 533–541, (1993).
Stevens et al., *Biol. Abstr.,* 86(3), Ref. No. 28429.

*Primary Examiner*—Marianne Porta Allen
*Attorney, Agent, or Firm*—Julia E. Abers

[57] ABSTRACT

A method for refolding recombinant platelet-derived growth factor from a high expression host cell system, such as *E. coli*, is provided in accordance with the present invention. The recombinant platelet-derived growth factor is isolated from inclusion body proteins, after which the free sulfydryl groups of the reduced monomeric recombinant protein are blocked. The blocked recombinant protein can then be brought into a biologically active conformation, without interference from the formation of incorrect disulfide bonds. Once in a biologically active conformation, the recombinant platelet-derived growth factor may be unblocked to allow the desired disulfide bonds to form, thus locking the recombinant protein into a biologically active conformation. The present invention also provides a novel mixed disulfide intermediate wherein the free sulfhydryl groups of reduced recombinant platelet-derived growth factor are derivatized to a disulfide blocking agent.

3 Claims, 18 Drawing Sheets

```
                                                                               60
1   CTAGAAGGAGGAATAACATATGTCTCTGGGTTCGTTAACCATTGCGGAACCGGCTATGAT
    ----+----+----+----+----+----+----+----+----+----+----+----+
    GATCTTCCTCCTTATTGTATACAGAGACCCAAGCAATTGGTAACGCCTTGGCCGATACTA
                         MetSerLeuGlySerLeuThrIleAlaGluProAlaMetIl
                         1

120
61  TGCCGAGTGCAAGACACGAACCGAGTGTTCGAGATCTCCCGGCCTCATCGACCGCAC
    ----+----+----+----+----+----+----+----+----+----+----+----+
    ACGGCTCACGTTCTGTGCTTGGCTCCACAAGCTCTAGAGGGCCGGAGTAGCTGGCGTG
    eAlaGluCysLysThrArgThrGluValPheGluIleSerArgArgLeuIleAspArgTh
    14

180
121 CAATGCCAACTTCCTGGTGTGCCCCTGCGTGCAGGTGCAGCCTGCTCCGGCTGTTG
    ----+----+----+----+----+----+----+----+----+----+----+----+
    GTTACGGTTGAAGGACCACACGGGGACGCACCTCCACGTCGGACGAGGCCGACAAC
    rAsnAlaAsnPheLeuValTrpProProCysValValGlnArgCysSerGlyCysCy
    34
```

FIG.1A

```
181  CAACAACCGCAAGTGCCAGTGCCGGGCCCCACCAGTGTGCAGCTGCGGGCCCAGTCCAGGTGAG  240
     GTTGTTGGCGTTGCACGTCACGGCCCGGGGTGGTCCACGTCGACGCCCGGGTCAGGTCCACTC
     sAsnAsnArgLysValGlnCysArgAsnValGlnLeuArgProThrGlnValGlnLeuArgProValGlnValAr
     54

241  AAAGATCGAGATTGTGCGGAAGAAGCCAATCTTTAAGAAGCCACGGTGACGCTGGAGGA      300
     TTTCTAGCTCTAACACGCCTTCTTCGGTTAGAAATTCTTCCGGTGCCACTGCGACCTCCT
     gLysIleGluIleValArgLysLysProIlePheLysLysAlaThrValThrLeuGluAs
     74

301  CCACCTGGCATGCAAGTGTGAGACAGTGGCAGCTGCACGGCCTGTGACCCGAAGCCCGGG    360
     GGTGGACCGTACGTTCACACTCTGTCACCGTCGACGTGCCGGACACTGGGCTTCGGGCCC
     pHisLeuAlaCysLysCysGluThrValAlaAlaAlaArgProValThrArgSerProGl
     94

361  GGGTTCCCAGGAGCAGCGATAAG
     CCCAAGGGTCCTCGTCGCTATTCTTAA
     yGlySerGlnGluGlnArg
     114       119
```

FIG.1B

```
         10                   30                   50
          .         .          .         .          .         .
1   TATGTCTATCGAAGAAGCGGGTACCCGCTGTCTGCAAGACCAGGACGGTCATTTACGAGAT  60
    ----+----+----+----+----+----+----+----+----+----+----+----+
    ACAGATAGCTTCTTCGCCCATGGGCGACAGACGTTCTGGTCCTGCCAGTAAATGCTCTA
    MetSerIleGluGluAlaValProAlaValCysLysThrArgThrValIleTyrGluIl
      1

70                  90                   110
          .         .          .         .          .         .
61  TCCTCGGAGTCAGGTAGACCCCACGTCCGCCAACTTCCTGATCTGGCCCGTGCTGGA     120
    ----+----+----+----+----+----+----+----+----+----+----+----+
    AGGAGCCTCAGTCCATCTGGGGTGCAGGCGGTTGAAGGACTAGACCGGGCACGACCT
    eProArgSerGlnValAspProThrSerAlaAsnPheLeuIleTrpProProCysValGl
              20

130                 150                  170
          .         .          .         .          .         .
121 GGTGAAACGCTGCACCGGCTGCTGCAACAGAGCAGTGTCAAGTGCCAGCCCTCGAGAGT    180
    ----+----+----+----+----+----+----+----+----+----+----+----+
    CCACTTTGCCGACGTGGCCGACGACGTTGTCTCGTCACAGTTCACGGTCGGGAGCTCTCA
    uValLysArgCysThrGlyCysCysAsnThrSerSerValLysCysGlnProSerArgVa
                                 40
```

FIG.5A

```
181  CCACCACCGCAGGTCAAGGTGGCCAAGGTGGAATACGTCAGGAAGAAGCCAAAATTAAA  240
     ----+----+----+----+----+----+----+----+----+----+----+----+
     GGTGGTGGCGTGCAGTTCCACCGGTTCCACCTTATGCAGTCCTTCTTCGGTTTTAATTT
     1HisHisArgSerValLysValAlaLysValGluTyrValArgLysLysProLysLeuLy
                  60

241  AGAAGTCCAGGTGAGGTTAGAGGAGCATTTGGAGTGCGCCTGCCGACCACAAGCTTGAA  300
     ----+----+----+----+----+----+----+----+----+----+----+----+
     TCTTCAGGTCCACTCCAATCTCCTCGTAAACCTCACGCGGACGGCTGGTGTTCGAACTT
     sGluValGlnValArgLeuGluGluHisLeuGluCysAlaCysAlaThrThrSerLeuAs
                  80

301  TCCGGATTATCGGAAGAGAGGACACGGGAAGGCCTAGGGAGTCAGGTAAAAACGGAAAAG  360
     ----+----+----+----+----+----+----+----+----+----+----+----+
     AGGCCTAATAGCCCTTCTCTCCTGTGCCCTTCCGGATCCCTCAGTCCATTTTTGCCTTTTC
     nProAspTyrArgGluGluAspThrGlyArgProArgGluSerGlyLysArgLysAr
                 100

361  AAAAAGGTTAAACCCACCTAATAG  389
     ----+----+----+----+----
     TTTTTCCAATTTGGGTGGATTATCCTAG
     gLysArgLeuLysProThr
                 120    125
```

FIG.5B

Non-Reduced    Reduced 1  2  3  4     5  6  7  8

Lanes #1 & #8 Fractions 26-28
Lanes #2 & #7 Fractions 30-32
Lanes #3 & #6 Fractions 33-35
Lanes #4 & #5 Fractions 36-37

Lanes #1 & #8 Fractions 26-28
Lanes #2 & #7 Fractions 30-32
Lanes #3 & #6 Fractions 33-35
Lanes #4 & #5 Fractions 36-37

```
            10                  30                 50
            .         .          .         .         .         .
  1   CTAGAAGGAGGAATAACATATGAGCCTGGGTTCCCTGAGCGTTGCCGAGCCAGCCATGAT      60
      ----+----+----+----+----+----+----+----+----+----+----+----+
      GATCTTCCTCCTTATTGTATACTCGGACCCAAGGGACTCGCAACGGCTCGGTCGGTACTA
                       MetSerLeuGlySerLeuSerValAlaGluProAlaMetIl
                                                               110

70                  90                 110
            .         .          .         .         .         .
 61   TGCCGAGTGCAAGACACGAACCGAGTGTTCGAGATCTCCCGGCCTCATCGACCGCAC       120
      ----+----+----+----+----+----+----+----+----+----+----+----+
      ACGGCTCACGTTCTGTGCTTGGCTCCACAAGCTCTAGAGGGCCGGAGTAGCTGGCGTG
      eAlaGluCysLysThrArgThrGluValPheGluIleSerArgArgLeuIleAspArgTh
                       130                        150                170

130                 150                170
            .         .          .         .         .         .
121   CAATGCCAACTTCCTGGTGTGGCCCCGGTGGAGGTGCCTCCGGCTCTTC               180
      ----+----+----+----+----+----+----+----+----+----+----+----+
      GTTACGGTTGAAGGACCACACCGGGGCCACCTCCACGTTCGCGACGAGGCCGAGAAG
      rAsnAlaAsnPheLeuValTrpProProSerValGluValGlnArgCysSerGlySerSe
                       190                        210                230

190                 210                230
            .         .          .         .         .         .
181   CAACAACCGCAACGTGCAGTGCCGGCCACCCAGGTGCCAGTCCAGGTGAG              240
      ----+----+----+----+----+----+----+----+----+----+----+----+
      GTTGTTGGCGTTGCACGTCACGGCCGGTGGGTCCACGGCCGGTCAGGTCCAGGTCCACTC
      rAsnAsnArgAsnValGlnCysArgProThrGlnLeuArgProValGlnValAr
```

FIG.10A

```
241 AAAGATCGAGATTGTGCGGAAGAAGCCAATCTTTAAGAAGGCCACGGTGACGCTGGAGGA 300
    ----+----+----+----+----+----+----+----+----+----+----+----+
    TTTCTAGCTCTAACACGCCTTCTTCGGTTAGAAATTCTTCCGGTGCCACTGCGACCTCCT
    gLysIleGluIleValArgLysLysProIlePheLysLysAlaThrValThrLeuGluAs
                    310                     320                 330

301 CCACCTGGCAATGCAAGTCTGAGATAGTGGCAGCTGCACGGGCTGTGACCTGAAGCCCGGG 360
    ----+----+----+----+----+----+----+----+----+----+----+----+
    GGTGGACCGTTACGTTCAGACTCTATCACCGTCGACGTGCCCGACACTGGACTTCGGGCCC
    pHisLeuAlaCysLysSerGluIleValAlaAlaAlaArgAlaValThrEndSerProGl
                    370                     380                 390

361 TACCGAGCTCGAATTCGGTACCATGGAAGCTTACTCGAGGATCCCGGGATAA       412
    ----+----+----+----+----+----+----+----+----+----+--
    ATGGCTCGAGCTTAAGCCATGGTACCTTCGAATGAGCTCCTAGGGCCCTATT
    yThrGluLeuGluPheGlyThrMetGluAlaTyrSerArgIleArgGlyEnd
                    400                     410

FIG.10B
```

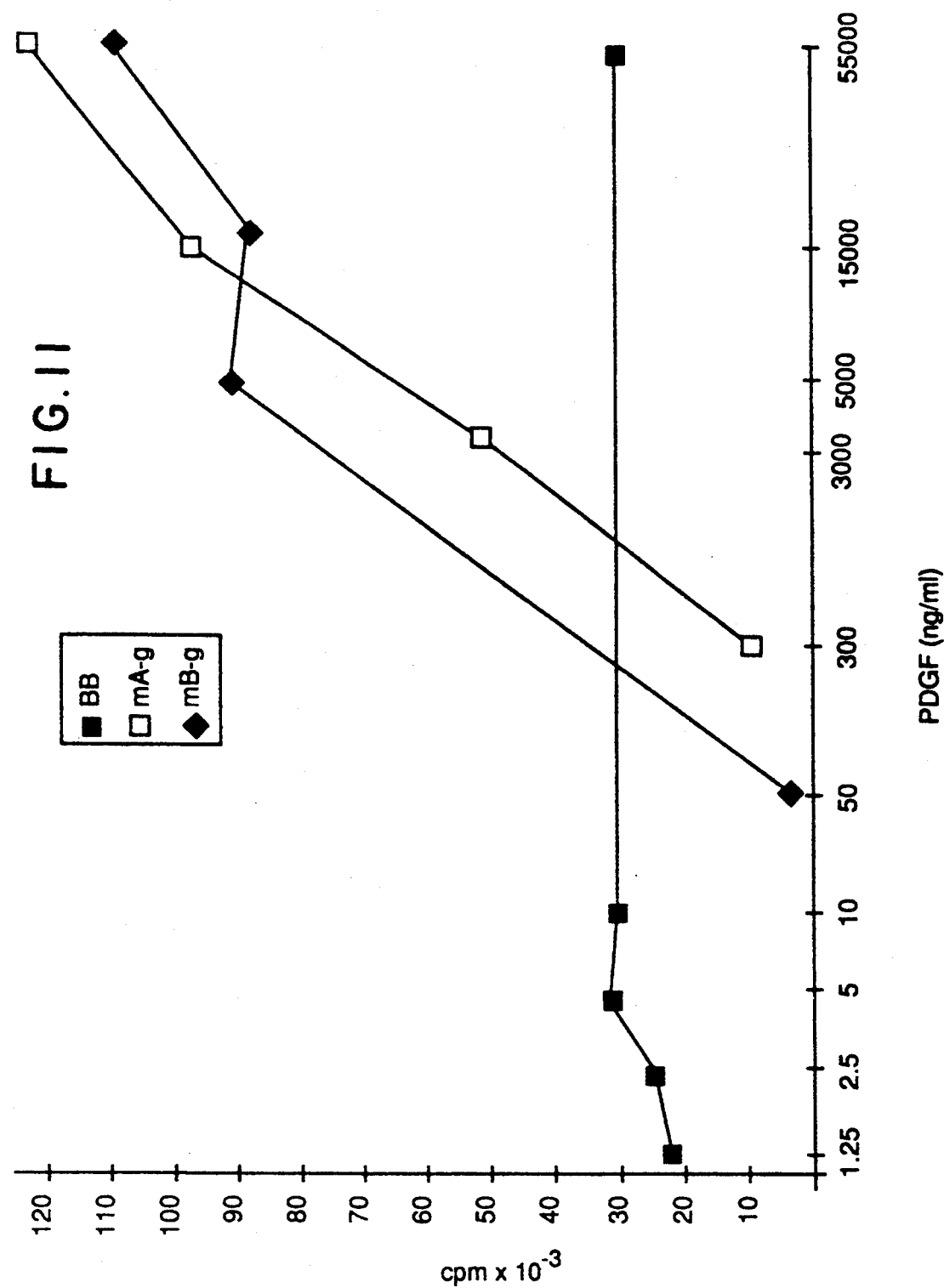

PRODUCTION OF PLATELET-DERIVED GROWTH FACTOR B-CHAIN HETERODIMERS FROM HIGH EXPRESSION HOST CELL SYSTEM

BACKGROUND

This application is a continuation of application Ser. No. 07/623,671, filed Dec. 2, 1990, which is hereby incorporated by reference, now abandoned, which is a continuation-in-part application of U.S. application Ser. No. 451,485, filed Dec. 15, 1989, now abandoned.

Advances in recombinant DNA technology in recent years have made possible the production of significant quantities of foreign proteins of interest in host cells. Recombinant proteins are produced in host cell systems by transfecting the host cells with DNA coding for the protein of interest, and then growing the transfected host cells under conditions which favor expression of the new recombinant protein by the host cell. Where the recombinant protein of interest is highly expressed by a particular host cell system, these exogenous proteins are typically precipitated within the host cell as inclusion bodies. High levels of expression, and consequent deposition of the recombinant protein in the form of inclusion bodies, is more likely to occur where procaryotic host cells are employed.

The procaryote *E. coli* is commonly selected for use in high expression systems, in part, because *E. coli* host cells tend to be more amenable to the production of extremely large quantities of recombinant protein. Low expression host cell systems, typically those employing eucaryotic host cells and yeast host cells, fail to produce recombinant protein in the tremendous quantities generated in high expression host cell systems. While expressed in relatively low quantities, however, recombinant proteins from these lower expression host cells are more likely to be recovered in their biologically active form, due to the tendency of low expression host cells to secrete the exogenous recombinant protein into the aqueous medium surrounding the host cell, rather than to deposit the protein in the high density inclusion bodies.

The trade-off with higher expression systems is that, in return for obtaining higher yields of recombinant product, the recombinant protein must be isolated from inclusion bodies. This typically requires refolding of the denatured protein in order to generate biologically active product. Both the difficulty and the success of efforts to refold recombinant proteins varies significantly with the particular protein being produced.

One recombinant protein which has become of particular interest in the wake of recent advances in recombinant DNA technology is a growth factor known as platelet-derived growth factor (PDGF). PDGF was initially described by Ross et al, *Proc. Natl. Acad. Sci. USA*, 71, 1207–1210 (1974), as a factor found in whole blood serum (but not platelet-poor serum) which is capable of supporting the growth of fibroblasts in culture. Human PDGF is now believed to be a major mitogenic protein in serum.

PDGF has been isolated from platelets and from serum. The native unreduced PDGF has been identified as a 27–35 kd mw dimeric protein. The variation in the number of bands observed on some separating gels may be due to glycosylation differences, protease action, or the presence of more than one molecular species. Reduction of PDGF yields two or more smaller bands on gels, in a molecular weight range of 10–18 kd. These smaller bands are believed to represent two smaller, dissimilar monomeric subunits of approximately 18 kd and 16 kd molecular weights called, respectively, the "A" and "B" subunits, or alternatively, PDGF A chain and PDGF B chain. The amino acid sequences of the two subunits of PDGF have been described, with the amino acid sequence of the PDGF B chain being identified as being more than 90% homologous with the predicted protein product of v-sis, the oncogene contained within the oncogenic simian sarcoma virus (SSV). Doolittle et al, *Science*, 221, 275–276 (1983), and Waterfield et al, *Nature*, 304, 2810–2814 (1983). The A chain has been found to be approximately 60% homologous to the B chain.

PDGF is believed to be biologically active only in dimeric form. These biologically active PDGF dimers can take the form of a PDGF-AB heterodimer, a PDGF-BB homodimer, or a PDGF-AA homodimer. Hannink et al, *Mol. Cell. Biol.*, 6, 1304–1314 (1986). Each monomeric subunit of the biologically active dimer, irrespective of whether it is an A chain monomer or a B chain monomer, contains eight cysteine residues. Some of these cysteine residues form interchain disulfide bonds which hold the dimer together.

The difficulty inherent in obtaining biologically active recombinant proteins from high expression host cell systems is, in the case of PDGF, further exacerbated by: (1) the large number of free cysteine residues in each PDGF monomer; (2) the dimeric form of the naturally occurring biologically active PDGF; and, (3) the extreme hydrophobicity of PDGF. As is expected with high expression systems, recombinant PDGF (rPDGF) produced in *E. coli* is predominantly found in inclusion bodies as the denatured monomer. Because of the limited solubility of this denatured rPDGF in aqueous solutions, it tends to aggregate before it can refold into its biologically active conformation, resulting in poor refolding efficiencies and, hence, poor yields of biologically active rPDGF material. Much of the isolated material may be partially denatured and partially misfolded, due either to original misfolding in the bacterial host cell and/or to inclusion body isolation conditions.

Recombinant PDGF, v-sis gene products, and analogs thereof, have been expressed in eucaryotic cells tranformed with vectors including exogenous genes, with varying degrees of success. U.S. Pat. No. 4,766,073 ("Murray et al I") (yeast host cells); Hannink et al, ibid; (COS-1 host cells); Hannink et al, *Mol. Cell. Biol.*, 6, 1343–1348 (1986) (COS-1 host cells); King et al, *Proc. Int'l Acad. Sci. USA*, 82, 5295–5299 (1985) (NIH 3T3 mouse host cells); Clarke et al, *Nature*, 308, 464 (1984) (NIH 3T3 mouse host cells); and, Gazit et al, *Cell*, 39, 89–97 (1984) (NIH 3T3 mouse host cells). However, none of these references disclose expression of more than 50 ng/mL of active PDGF in culture media. More recently, yields of approximately 200 to 1000 ng/mL have been reported from yeast host cell systems. U.S. Pat. No. 4,845,075 ("Murray et al II"). International Patent Application No. PCT/US88/00701 discloses the production of PDGF in Chinese Hamster Ovary (CHO) cells in amounts of approximately 1 μg/mL.

There have been infrequent accounts of the expression of v-sis gene products in procaryotes. For example, Devare et al, *Pro. Natl. Acad. Sci. USA*, 79, 3179–3182 (1982), reported to have expressed p28$^{sis}$ in *E. coli* and detected it immunologically. This *E. coli*-produced p28$^{sis}$ was not reported to be biologically active. Wang et al, *J. Biol. Chem.*, 259, 10645-10648 (1984), reported an observation that p28$^{sis}$ expressed as a fusion protein in *E. coli*, competed with iodinated human platelet PDGF for binding to the PDGF receptor. The *E. coli*-produced recombinant protein was, however, in this instance isolated from a soluble fraction containing approximately 10% of the total expressed recombinant protein, and was not demonstrated to possess mitogenic or chemotactic activity. The vastly predominant (90%) insoluble inclusion body form of the recombinant protein was discarded, and presumably biologically inactive. More recently, Hoppe et al, *Biochemistry*, 28, 2956-2960 (1989), disclosed the expression of a rPDGF B fusion protein cleavage product from *E. coli*, with subsequent refolding resulting in a yield of approximately 0.7 mg. of refolded rPDGF B homodimer analog per liter of fermentation broth.

For commercial purposes, however, it has historically been favored to obtain rPDGF from low expression host cell systems because of the expected secretion of the rPDGF from these systems in its correctly folded, biologically active dimeric form. This line of thinking has prevailed notwithstanding the attainment of only small quantities of the recombinant protein from these systems. Procaryotic hosts, on the other hand, have not been expected to be able to produce active rPDGF. Kelly et al, *EMBO J.*, 4(13A), 3399-3405 (1985). Even where rPDGF exhibiting specific binding activity has been obtained from *E. coli* (Wang et al, ibid), the *E. coli* host cell system used was not a particularly high expression system, and only the small soluble fraction (approximately 10%) of the total recombinant protein was recovered. Moreover, there was no demonstration by this *E. coli*-produced rPDGF of either the mitogenic or chemotactic activity required for effective therapeutic use of the recombinant protein.

With respect to recombinant proteins in general, however, refolding methods have been used for transforming denatured recombinant proteins into their active form. U.S. Pat. Nos. 4,511,503 and 4,518,256, for example, describe three refolding procedures which are generally applicable, with only minor modifications, to the recovery of biologically active recombinant proteins from inclusion bodies. These procedures recognize that the tertiary, or refolded, structure of proteins is stabilized by hydrogen bonding, hydrophobic interactions, and ionic bonding between amino acid moieties of the protein. When present, it is the disulfide bonding between cysteine moieties which "locks" the tertiary structure in place. These methods therefore seek to eliminate random disulfide bonding prior to coaxing the recombinant protein into its biologically active conformation through its other stabilizing forces.

In one approach, the denatured protein of interest is further purified, under reducing conditions which maintain the cysteine moieties of the protein as free sulfhydryl groups, by supplying a reducing agent throughout all of the purification steps. This permits the protein to refold itself under the conditions of purification, in the absence of incorrect disulfide bond formation. The reducing agent is then diluted into an aqueous solution to enable the refolded protein to form the appropriate disulfide bonds in the presence of air or some other oxidizing agent. This enables refolding to be easily incorporated into the overall purification process. This method is most effective for recombinant proteins which have relatively uncomplicated tertiary structures in their biologically active forms.

In another approach, refolding of the recombinant protein is allowed to occur in the presence of both the reduced (R—SH) and oxidized (R—S—S—R) forms of a sulfhydryl compound. This enables free sulfhydryls and disulfides to be constantly formed and reformed throughout the purification process. The reduced and oxidized forms of the sulfhydryl compound are provided in a buffer having sufficient denaturing power that all of the intermediate conformations of the protein remain soluble in the course of the unfolding and refolding. Urea is suggested as a suitable buffer medium because of its apparent ability to act as both: (1) a weak enough denaturing agent to allow the protein to approximate its correct conformation; and, (2) a strong enough denaturant that the refolding intermediates maintain their solubility. This approach also works best where the recombinant inclusion body proteins of interest have relatively uncomplicated folding patterns.

A third approach, which is used in more difficult refolding situations, is designed to first break any disulfide bonds which may have formed incorrectly during isolation of the inclusion bodies, and then to derivatize the available free sulfhydryl groups of the recombinant protein. This is accomplished by sulfonating the protein to form a protein-S—SO$_3$ bond. The resulting protein-S-sulfonate solution is then diluted into an aqueous solution where proper refolding is allowed to occur in the absence of incorrect disulfide bond formation. A system containing a sulfhydryl compound (R—SH) and a small percentage of its corresponding oxidized form (R—S—S—R), is then added to the aqueous solution. The pH is adjusted (raised) to a value such that the sulfhydryl compound (R—SH) is at least partially in ionized form (R—S—) so that nucleophilic displacement of the sulfonate is enhanced. While the sulfhydryl compound is sufficient to effect conversion of the protein-S-sulfonate to the appropriate disulfide binding partner, the presence of an oxidized form is required to insure that suitable disulfide bonds will remain intact.

Hoppe et al reported some success refolding rPDGF analog using a method based on this last approach. However, because of the inordinately high number of sulfhydryl groups of PDGF, namely eight per monomer, it remains difficult, at best, to control the refolding of rPDGF so that disulfide bond formation takes place only after the rPDGF has assumed a biologically active conformation. For example, Hoppe et al found it necessary to add urea to solubilize the sulfonated rPDGF fusion protein cleavage product in order to achieve a 0.7 mg/L yield.

Accordingly, it is an object of the present invention to provide a streamlined method for isolating and purifying biologically active recombinant rPDGF from high expression host cell systems.

SUMMARY OF THE INVENTION

The present invention provides a method for refolding reduced rPDGF from a high expression host cell system, such as *E. coli*. A mixed disulfide bond is formed between the free sulfhydryl groups of the reduced monomeric PDGF and a disulfide blocking agent, having the formula R—S—S—R, to form a novel blocked monomeric rPDGF intermediate. The blocked rPDGF monomer is then brought into a biologically active conformation, after which the mixed disulfide bonds of the blocked rPDGF may be broken, so that the desired disulfide bonds can form between reduced rPDGF cysteine residues to lock the rPDGF into a biologically active dimeric or monomeric conformation. The present invention further provides novel biologically active PDGF monomers.

BRIEF DESCRIPTION OF THE DRAWINGS

FIG. 1 is a diagram of the coding sequence used to express rPDGF $B_{119}$ in *E. coli* expression vector pCFM1156, as set forth in Example 1.

FIG. 5 is a diagram of the coding sequence used to express rPDGF $A_L$ in *E. coli* expression vector pCFM1156, as set forth in Example 5.

FIG. 10 is a diagram of the coding sequence used to express rPDGF $B_{109}$ [$Ser^{43}$,$Ser^{52}$,$Ser^{53}$,$Ser^{99}$] analog in *E. coli* expression vector pCFM1156, as set forth in Example 9. The stop codons at position 110 of PDGF B and downstream in pCFM1156 are shown, along with the translation products which result with and without "readthrough" of the first stop codon.

FIG. 11 demonstrates the activity of the monomeric mixed disulfide intermediates of PDGF $B_{119}$ amd PDGF $A_L$, as compared with PDGF $B_{119}$ homodimer.

DETAILED DESCRIPTION OF THE INVENTION

Figure 2:
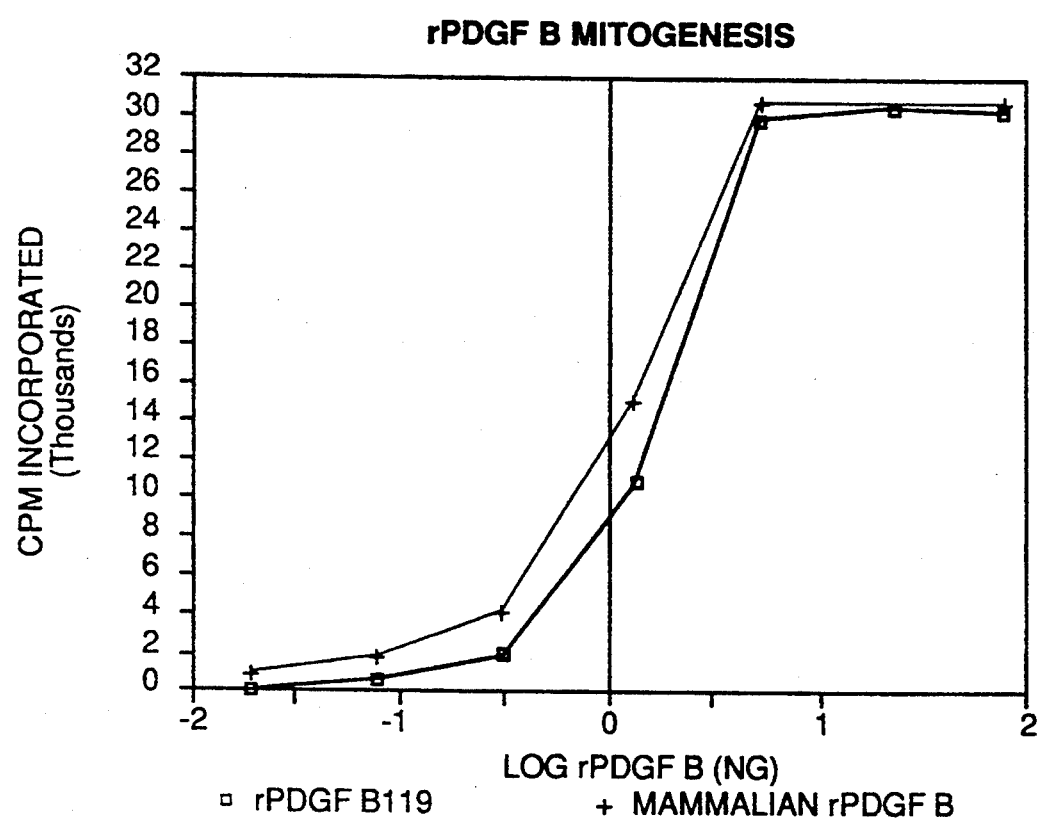
FIG. 2 is a graph showing the mitogenic activity of *E. coli*-produced rPDGF $B_{119}$ which has been refolded in accordance with the teachings of the present invention.

The present invention provides a novel method for the isolation, refolding, and purification of rPDGF from *E. coli* or other high expression host cell systems. The method of the present invention greatly increases refolding efficiencies in obtaining biologically active dimeric or monomeric rPDGF, resulting in much higher yields of the active rPDGF from inclusion bodies than are obtained from prior art methods.

A disulfide blocking agent is used in the purification process in order to refold reduced monomeric PDGF, obtained from *E. coli* or other procaryotes, into its active conformation. The blocking agent of the present invention forms a novel monomeric mixed disulfide intermediate with the free sulfhydryls of the cysteine moieties of reduced, or unfolded monomeric PDGF. This mixed disulfide intermediate ties up substantially all of the free sulfhydryls of reduced PDGF, and thus prevents the premature, or untimely, formation of internal disulfide bonds during isolation and purification of the reduced rPDGF. At the same time, this modification also renders the rPDGF intermediate soluble in aqueous solutions.

In order to aid in the understanding of the present invention, the following terms, as used herein, have the definitions designated below.

Unless otherwise specified, PDGF is any combination of PDGF monomers and/or dimers, including analogs thereof, reduced or unreduced, biologically active, or inactive, recombinant or otherwise. The term "PDGF" is intended to include PDGF analogs having one or more modifications to the number and/or identity of amino acid sequences of naturally occurring PDGF.

The terms "PDGF monomer" and "monomeric PDGF" mean a single monomeric PDGF molecule which is not disulfide bonded to any other PDGF molecule. It will be appreciated that "reduced PDGF" will necessarily be monomeric PDGF.

The terms "PDGF dimer" or "dimeric PDGF" mean a PDGF molecule comprising two monomeric PDGF subunits which are disulfide bonded to each other.

The term "biologically active PDGF dimer" means dimeric PDGF having substantially the same mitogenic activity and/or chemotactic activity as naturally occurring PDGF.

The term "biologically active PDGF monomer" means monomeric PDGF having a specific mitogenic activity of at least about one-one thousandth the mitogenic activity of naturally occurring dimeric PDGF.

The term "biologically active conformation", as used herein, refers to the conformation of a biologically active PDGF dimer or a biologically active PDGF monomer.

As used herein, "refolding" means bringing reduced or partially reduced PDGF into a biologically active conformation. Refolding includes those instances wherein rPDGF has been produced in denatured form and is, in fact, being brought into a biologically active conformation for the first time. The term "refolding" may be used interchangeably with "folding". The term "refolded" refers to PDGF which has been brought into a biologically active conformation.

The "blocking agent" used herein is a disulfide compound, having the formula R—S—S—R, which is capable of forming disulfide derivatives with the free sulfhydryls of the cysteine moieties of reduced, or unfolded PDGF.

The term "mixed disulfide" refers to a disulfide bond formed between a reduced cysteine moiety of monomeric PDGF and one of the R moieties of the blocking agent. The term "mixed disulfide" specifically includes the situation wherein R is cysteine, and, therefore, cysteine moieties appear on either side of the disulfide bond.

The term "mixed disulfide intermediate" refers to a derivatized PDGF monomer wherein substantially all of the sulfhydryl groups of the PDGF monomer are derivatized to an R moiety of the blocking agent through a mixed disulfide bond. In other words, there is an insufficient number of free sulfhydryls available for the formation of internal disulfide bonds.

As used herein "interchain disulfide bond" is a disulfide bond formed between two cysteine moieties of a PDGF dimer, wherein the cysteine moieties which form the disulfide bond are from different monomeric subunits.

In contrast, an "intrachain disulfide bond" is a disulfide bond formed between two cysteine moieties of a PDGF dimer or monomer, wherein the cysteine moieties which form the disulfide bond are from the same monomeric subunit.

The refolding method of the present invention makes use of a blocking agent which blocks the free sulfhydryl moieties of the reduced monomeric PDGF such that these moieties are rendered incapable of forming intrachain and interchain disulfide bonds. Once the sulfhydryl moieties of the PDGF monomer have been blocked, the rPDGF is refolded into a biologically active conformation. This may be followed by elimination of the blocking agent, so that the favored intrachain and interchain disulfide bonds can form to lock the PDGF into its biologically active conformation. In most cases, this results in a biologically active dimer. However, where a PDGF analog has been made to omit cysteine residues required for interchain disulfide bonding, elimination of the blocking agent results in a biologically active monomer. The refolding method of the present invention is particularly useful for refolding rPDGF from inclusion bodies.

Generally, the blocking agents of the present invention are disulfide compounds having the formula R—S—S—R, wherein R is a soluble organic group. Representative soluble organic groups include, but are not limited to, γ-glutamyl-cysteinyl-lysine (R—S—S—R is oxidized glutathione), cysteine (R—S—S—R is oxidized cysteine), and glycolic acid. What is important in the selection of a disulfide compound for use as a blocking agent in the present invention is that the disulfide compound be capable of forming a mixed disulfide with the cysteine moieties of PDGF. Preferably, the blocking agent is selected from the group consisting of oxidized cysteine (Cys-S—S-Cys) and oxidized glutathione (G—S—S—G). More preferably, the blocking agent is oxidized glutathione.

The blocking agent of the present invention modifies, or blocks, substantially all of the free sulfhydryl groups of reduced PDGF by oxidizing these sulfhydryls to form a mixed disulfide bond between the blocking agent (R—S—S—R) and PDGF (PDGF-SH), resulting in the novel monomeric intermediate (rPDGF-S—S—R) of the present invention. For example, the mixed disulfide bonds may form between reduced rPDGF monomer and oxidized cysteine (to form a rPDGF-S—S-Cys intermediate) or between reduced rPDGF monomer and oxidized glutathione (to form a rPDGF-S—S—G intermediate). In light of the limited success of prior art methods in refolding active rPDGF from inclusion bodies, it has surprisingly been found that the blocking of the free sulfhydryls of reduced rPDGF, in accordance with the teachings of the present invention, is able to successfully prevent the premature, or untimely, formation of internal disulfide bonds during isolation, purification, and refolding of inclusion body-derived rPDGF, while at the same time rendering the derivatized rPDGF monomer soluble in aqueous solutions.

Once rPDGF has been blocked (i.e., the monomeric mixed disulfide intermediate of the present invention has been formed), conditions are specifically selected to promote the folding of the PDGF-S—S—R intermediate into a biologically active conformation. Because the mixed disulfide intermediate of the present invention, unlike reduced unblocked PDGF, is soluble in aqueous solutions, it is believed to be possible to take advantage of the forces present in a non-denaturing aqueous environment to induce the monomeric intermediate, or blocked rPDGF, into a biologically active conformation without interference from random disulfide bond formation. At such time as a biologically active conformation is achieved, the blocked PDGF-S—S—R is unblocked.

Surprisingly, the blocked monomeric PDGF intermediate of the present invention has been found to exhibit biological activity, although a significantly greater quantity of the monomer is required to achieve the maximal activity observed for the naturally occurring PDGF dimer (i.e., the specific activity of the monomer is lower than that of the dimer). PDGF monomer is not believed to naturally exist in monomeric form, and thus has not been isolated from nature. The dimeric form of PDGF has been hypothesized as being necessary for biological activity on the basis of current models of the mechanism whereby PDGF is thought to transmit a signal via interaction with PDGF cell surface receptors.

The prevailing model for the required interaction with cell surface receptors suggests that two PDGF receptors must interact with each other in order to transmit the signal. This results in a mutual reaction called cross-phosphorylation; i.e., each receptor catalyzes the addition of a phosphate group to the other. Each monomeric subunit of a PDGF dimer is believed to bind to a single receptor molecule, thus bringing two receptors together and permitting the cross-phosphorylation, sometimes referred to as receptor dimerization. Williams, *Science*, 243, 1564–1570 (1989); Hammacher et al, EMBO, 8, 2489–2495 (1989). Although it has subsequently been suggested that the monomeric form of PDGF may, in some cases., exhibit biological activity (International Patent Application No. 89/04460), the existence of any such activity in a PDGF monomer has not heretofor been shown to exist. Furthermore, no explanation has been provided for how a monomer might induce the required receptor dimerization.

Unblocking of the monomeric PDGF-S—S—R intermediate of the present invention can result in either a biologically active PDGF dimer or a biologically active PDGF monomer. The latter may be obtained by means of a PDGF analog, wherein one or more of the cysteine residues required for the formation of interchain disulfide bonds have been substituted with other amino acids. Where an analog of this type is desired, the amino acids which are substituted for the cysteine residues are preferably uncharged amino acids. More preferably, the uncharged amino acids are serine residues.

Like the novel blocked monomeric mixed disulfide intermediate of the present invention, the unblocked monomeric analog, obtained from unblocking of an appropriately selected mixed disulfide monomeric analog, results in a biologically active PDGF monomer. Although it was observed that substantially greater quantities of either of these forms of monomeric PDGF (i.e., mixed disulfide intermediate or unblocked analog) was required to exhibit the observed maximal biological activity achievable with dimeric forms of PDGF, it was also found that these monomers are, in fact, capable of achieving a level of "superactivity", that is, activity at least about 3 to 3.5 times higher than that achievable with any amount of dimer.

Preferably, unblocking is accomplished by bringing the blocked PDGF-S—S—R intermediate into contact with a reduced sulfhydryl compound. More preferably, the reduced sulfhydryl compound is cysteine. Addition of the reduced sulfhydryl compound initiates disulfide interchange, which results in the unblocking of the mixed disulfide bonds and, in turn, the consequent formation of the favored intrachain and/or interchain disulfide bonds. Formation of these disulfide bonds, which define the tertiary structure of PDGF (intrachain and interchain bonds) and hold the dimeric form together (interchain bonds), is delayed or impeded until such time as the rPDGF can be manipulated into a biologically active conformation.

It has surprisingly been found that the method of the present invention can be used to form a type of dimeric rPDGF, otherwise referred to as a "mixed dimer" wherein the monomeric subunits of the dimeric rPDGF molecules are derived from different high expression host cells. For example, the present invention enables the production of rPDGF-AB heterodimer from inclusion body proteins. Moreover, unlimited possibilities exist for the preparation of rPDGF mixed dimers which are made up of distinctly different monomeric subunits, such as different chains (e.g., A and B-chains), different forms of chains (e.g., PDGF $B_{109}$ and PDGF B119), and different analogs. Each of the two different monomeric subunits which are selected to make up the desired mixed dimer are isolated from the respective different inclusion body proteins and then blocked in accordance with the teachings of the present invention. Relative amounts of the two different blocked monomeric subunits are then combined in a ratio that is determined to favor formation of the desired mixed dimer. The favored ratios will be apparent to those skilled in the art. After allowing the blocked monomeric subunits to achieve a biologically active conformation, the monomeric subunits are unblocked, resulting in the formation of a mixed dimer.

More specifically, the method of the present invention may be used to refold *E. coli*-derived rPDGF, as follows. The inclusion body protein is first isolated from *E. coli* or other high expression host cell paste by any one of a number of methods known in the art. Preferably, the host cells containing rPDGF are first broken with a homogenizer, such as a Menton-Gaulin or Microfluidizer homogenizer, at a pressure of 10,000 to 14,000 psi, preferably at 14,000 psi. In order to maintain the inclusion body rPDGF in its reduced monomeric state during isolation from the inclusion bodies, the host cells are preferably lysed at a pH of less than or equal to about 6 and at a temperature less than about 12° C. The resulting lysate may then be centrifuged, with large particles, including inclusion bodies, being spun down into a pellet. The supernatant is then poured off, with the pellet, containing reduced inclusion body rPDGF, being saved.

The inclusion bodies from the pellet must be solubilized. This may be accomplished by any of a number of known prior art methods. Some methods utilize a strongly denaturing medium, such as 4 to 6.5M guanidine.HCl. The inclusion bodies are preferably solubilized with a more mild denaturant, such as 4 to 9M urea, preferably 8M urea, with the pH then being adjusted downward by addition of HCl. Preferably, the pH is adjusted to between about 3.0 to 4.0, preferably about 3.0.

The inclusion body rPDGF proteins which have been isolated from the host cell paste are preferably purified prior to derivatization of the sulfhydryl groups. After the pH has been adjusted downward, the resulting solubilized, reduced monomeric rPDGF may be isolated and partially purified using any one of a number of protein purification techniques known in the art. Preferably, the monomeric rPDGF is purified using ion exchange chromatography, with the chromatographic step(s) preferably being carried out in the presence of 8M urea. In order to separate the rPDGF monomer from other components contained in the pellet, SE-Sepharose ® (Pharmacia, Uppsala, Sweden), or another suitable cationic exchanger, may be added batchwise into the solubilized inclusion body mixture. The SE-Sepharose ® binds the reduced rPDGF, with many of the remaining soluble and insoluble components being washed away. The pH may then be adjusted upward, preferably to about 7.6 with sodium hydroxide (NaOH), provided anaerobic or reducing conditions are used in order to maintain the rPDGF in its reduced monomeric state. Raising the pH removes additional contaminating proteins and allows the rPDGF monomer to be more easily removed from the resin. The resulting basic solution is subjected to gradient chromatography, again under anaerobic conditions, to isolate the unfolded rPDGF monomer The free sulfhydryl groups of the reduced rPDGF are then protected by blocking these groups through the formation of the monomeric rPDGF-S—S—R mixed disulfide intermediate of the present invention. Preferably, these steps are also carried out in the presence of 8M urea. Suitable blocking agents of the present invention, such as oxidized cysteine or oxidized glutathione, are added to the solubilized inclusion body mixture in the amount of approximately 0.1 to 0.2M, preferably about 0.1M. Similar molar amounts of other blocking agents may be used. The solution is then allowed to stir under anaerobic conditions for about 18 to about 24 hours, preferably about 18 hours, at about 22° C. to 26° C. preferably around 22° C. The precise ranges of concentrations and temperature which are most effective will depend upon the particular blocking agent selected for use with the present invention.

The resulting protected rPDGF-S—S—R monomer solution is then buffer exchanged into a non-denaturing buffer. This can be accomplished by first exchanging the solution containing the protected rPDGF-S—S—R monomeric intermediate with a solution containing urea (preferably about 8.0M) and acetic acid (preferably about 0.1M), then with acetic acid alone (preferably about 0.1M), before being diluted to between about 0.5 and 0.2 mg/mL, with a non-denaturing aqueous buffer. The non-denaturing aqueous buffer is believed to be conducive to proper refolding due to the forces present in the aqueous medium, under which the blocked monomeric rPDGF intermediate should tend to seek its biologically active conformation. Because the free sulfhydryl groups of the reduced rPDGF are protected within the monomeric rPDGF-S—S—R intermediate, the protein cannot be prematurely locked into an inactive conformation by the random formation of incorrect disulfide bonds. If Tris is used as the non-denaturing aqueous buffer, appropriate concentration ranges are 10 to 30 mM, preferably 20 mM. The pH is kept at approximately 7.5 to 8.5, with the addition of a suitable acid or base. Preferably the acid is HCl and the base is NaOH.

Disulfide exchange is then initiated by removal of the blocking agent moiety from the mixed disulfide which has formed between the blocking agent and the rPDGF monomer. Preferably, a reduced sulfhydryl compound (R—SH) is brought into contact with the blocked monomeric rPDGF intermediate to initiate unblocking. Suitable reduced sulfhydryl compounds include, but are not limited to, β-mercaptoethanol, reduced glutathione, and cysteine. What is important in selecting a reduced sulfhydryl compound is that the reduced sulfhydryl compound be able to displace the blocking agent moiety of the mixed disulfide. The reduced sulfhydryl is preferably reduced cysteine (Cys-SH). Where cysteine is added as the reduced sulfhydryl, the final concentration of cysteine is between about 0.5 and 3.0 mM. The mixture is incubated at about 0° C. to 37° C., preferably about 30° C., depending upon the blocking agent, for about 4 to about 24 hours, preferably about 16 hours. The solution may then be made about 0.1M in acetic acid before final purification.

The therapeutic application of biologically active PDGF dimers and/or biologically active PDGF monomers produced in accordance with the present invention can be used for the treatment of many types of wounds of mammalian species by physicians and/or veterinarians. The amount of biologically active PDGF used in such treatments will, of course, depend upon the severity of the wound being treated, the route of administration chosen, and the specific activity or purity of the PDGF, and will be determined by the attending physician or veterinarian. The term "PDGF therapeutically effective" amount refers to the amount of PDGF, in the absence of other exogenously applied growth factors, determined to produce a therapeutic response in a mammal. Such therapeutically effective amounts are readily ascertained by one of ordinary skill in the art.

The PDGF produced in accordance with the present invention may be administered by any route appropriate to the wound or condition being treated. Conditions which may be beneficially treated with therapeutic application(s) of PDGF include open dermal wounds, dermal incisional wounds, and gastointestinal incisional wounds. PDGF may also be used in the healing of bone, cartilage, tendons, ligaments, and epithelium (e.g., intestinal linings, stomach linings), and in glial repair.

Preferably, the PDGF is applied exogenously to the wound. The exogenous application may be by a single application or dose, or by a repeated dose at multiple designated intervals. Compositions for exogenous application of the PDGF of the present invention are readily ascertained by one of ordinary skill in the art. It will be readily appreciated by those skilled in the art that the preferred route will vary with the wound or condition being treated. While it is possible for the PDGF to be administered as the pure or substantially pure compound, it is preferable to present it as a pharmaceutical formulation or preparation.

The formulations of the present invention, both for veterinary and for human use, comprise a therapeutically effective amount of PDGF as above described, together with one or more pharmaceutically acceptable carriers therefore and optionally other therapeutic ingredients. The carrier(s) must be "acceptable" in the sense of being compatible with the other ingredients of the formulation and not deleterious to the recipient thereof. Desirably, the formulation should not include oxidizing or reducing agents and other substances with which peptides are known to be incompatible. The formulations may conveniently be presented in unit dosage form and may be prepared by any of the methods well known in the art. All methods include the step of bringing into association the active ingredient with the carrier which constitutes one or more accessory ingredients. In general, the formulations are prepared by uniformly and intimately bringing into association the PDGF with liquid carriers or finely divided solid cariers or both.

The following examples are provided to aid in the understanding of the present invention, the true scope of which is set forth in the appended claims. It is understood that modifications can be made in the procedures set forth, without departing from the spirit of the invention.

EXAMPLE 1

Production of rPDGF $B_{119}$

Any form of rPDGF B can be refolded from inclusion bodies using the method of the present invention. The 109 amino acid form, commonly recognized as the naturally occurring human form of PDGF B, can, for example, be refolded from *E. coli* host cells into a biologically active dimer or a biologically active monomer. A gene coding for a 119 amino acid form of human PDGF B, shown in FIG. 1, was selected for expression by *E. coli* host cells, because placement of a stop codon at amino acid 120 alleviates a stop codon "read through" problem observed when the stop codon is placed at amino acid 110, as more fully described in copending U.S. patent application Ser. No. 454,794, now U.S. Pat. No. 5,149,792 which is incorporated herein by reference.

The 119 form of PDGF B, or any other form of PDGF B, can be made synthetically, as is described with respect to the PDGF A set forth in Example 5. The PDGF B may also be derived using the closely homologous v-sis gene of simian sarcoma virus as a starting material. The PDGF $B_{119}$ in this example was made from the v-sis starting material.

Conversion of Amino Acids 101 and 107

One μg of the plasmid pC60, a clone of the simian sarcoma virus retroviral genome (Wong-Staal et al, *Science*, 213, 226–228 (1981), was digested with restriction endonucleases SalI and XbaI, with the resulting 1183 base pair fragment then being purified by electrophoretic separation in a low-melting temperature agarose gel, in accordance with the procedures described by Maniatis et al, *Molecular Cloning—A laboratory Manual*, Cold Spring Harbor Laboratory (1982). The purified fragment was then excised from the gel. At the same time, 0.2 μg of M13mp19 DNA was also digested with SalI and XbaI, with the large 7245 base pair band being similarly isolated from a low-melting temperature gel. Both excised gel slices were melted at 65° C., and then cooled to 37°. All of the gel with the 7245 base pair M13mp19 fragment and one fourth of the gel with the 1183 base pair v-sis fragment were mixed and ligated according to Struhl, *Biotechniques*, 3, 452–453 (1985). The ligated DNA was transformed into *E. coli* K12 strain TG1, and a clear plaque was selected and grown in liquid culture. The presence of the 1183 base pair v-sis fragment in the M13mp19 vector was confirmed by preparation of the RF form of the phage DNA and restriction map analysis. Messing et al, *Nucl. Acids Res.*, 9, 309–321 (1981).

The M13mp19/v-sis phage thus obtained was grown in liquid culture, and the single stranded DNA isolated. Messing et al, ibid. This DNA was used as a template for oligonucleotide-directed in vitro mutagenesis to convert the amino acids at residues 101 and 107 to the corresponding amino acids of PDGF B. I.e., the ATA codon coding for Isoleucine 101 was converted to ACA (coding for Threonine), and the GCT codon coding for Alanine 107 was converted to CCT (coding for Proline).

10 μg of the M13mp19/v-sis single-stranded DNA was annealed with 8 pmol of a phosphorylated oligonucleotide having the sequence:

5'GGTCACAGGCCGTGCAGCTG-CCACTGTCTCACAC 3'

This sequence is homologous to nucleotides 4283 to 4316 of the v-sis gene (numbering system of Devare et al, ibid). The underlined bases of the oligonucleotide denote the changes from the v-sis to the human PDGF B sequence. DNA synthesis was initiated on the mutant oligonucleotide, with the complete mutant strand being synthesized with the Klenow fragment of *E. coli* DNA polymerase I using thionucleotide triphosphates, followed by ligation with T4 DNA ligase. Any remaining single-stranded template M13mp18/v-sis DNA was removed by filtration on nitrocellulose filters. The non-mutant strand was nicked by incubation with restriction endonuclease III. The nicked non-mutant strand was then repolymerized with the deoxynucleotide triphosphates, using the mutant strand as a template. As a result, both DNA strands in the final product contained the desired mutations. The DNA was transformed into *E. coli* K12 strain TG1. Plaques were selected, grown in liquid culture, and the single-stranded DNA isolated. The DNA was sequenced by the method of Sanger et al, *Proc. Natl. Acad. Sci. USA*, 74, 5463–5467 (1977) to confirm that the desired mutants had been obtained.

Conversion of Amino Acids 6 and 7

In the next step, the 5' portion of the mutated v-sis gene was replaced with a synthetic DNA fragment which changed amino acids 6 and 7 from the v-sis to the human PDGF B forms. This synthetic fragment also provided a translation-initiating ATG codon immediately preceding the codon for Serine 1 of human PDGF B, as well providing sequences for binding to *E. coli* ribosomes and a restriction site for ligation into the desired *E. coli* expression vector (described below). The synthetic DNA fragment was ligated to the BglII site located at nucleotide 4061 of the v-sis gene (numbering system of Devare et al, ibid). Because a BglII site which is present within the M13mp19 vector would complicate and interfere with this step, the mutated v-sis gene was first moved to the commercially available plasmid vector pUC18, which does not contain a BglII site. The M13mp19/v-sis mutant RF DNA was restricted with SalI and BamHl, and the resulting 1193 base pair fragment isolated by electrophoresis using a low-melting temperature agarose gel. This fragment was ligated to the plasmid pUC18 which had also been restricted with SalI and BamH1. The ligated DNA was transformed into the commercially available *E. coli* K12 strain DH5 and transformants were selected by growth in the presence of ampicillin. Colonies were selected, grown in liquid culture, and isolated plasmid DNA analyzed by restriction mapping for the presence of the v-sis insert.

The pUC18/v-sis mutant DNA was restricted with HindIII, which cuts in the polylinker of pUC18 just upstream of the mutated v-sis insert, and with BglII, which cuts within the v-sis DNA at nucleotide 4061 (numbering system of Devare et al, ibid) corresponding to amino acid number 24 of the mature protein product. The large 3565 base pair fragment resulting from this reaction was isolated by electrophoresis in a low-melting temperature agarose gel. This fragment was ligated to a synthetic double-stranded DNA fragment with the following sequence:

```
5'AGCTTCTAGAAGGAGGAATAACATATGTCTCTGGGTTCGTTAACCATTGCG—
3'     AGATCTTCCTCCTTATTGTATACAGAGACCCAAGCAATTGGTAACGC—

—GAACCGGCTATGATTGCCGAGTGCAAGACACGAACCGAGGTGTTCGA  3'
—CTTGGCCGATACTAACGGCTCACGTTCTGTGCTTGGCTCCACAAGCTCTAG 5'
```

This synthetic DNA fragment contains a HindIII "sticky" end at its upstream (left) end and a BglII "sticky" end at its downstream (right) end. In addition, an XbaI site (TCTAGA) is present within the synthetic DNA just downstream of the HindIII "sticky" end, which allows subsequent restriction with XbaI for ligation into the XbaI site of an expression vector described below. The ligated DNA was transformed into *E. coli* K12 strain DH5, with transformants being selected by growth on ampicillin-containing medium. The plasmid DNAs from resulting colonies were analyzed by restriction mapping for the presence of the synthetic DNA fragment. At this point, the pUC18/v-sis construction contained a mutated v-sis gene, with amino acid numbers 6, 7, 101, and 107 changed to the human PDGF B form, and its 5' end altered to begin translation with an ATG codon immediately preceding Serine 1.

Conversion of Amino Acid 114 and Placement of Stop Codon at Amino Acid 120

In the next step, the codon for amino acid number 114 was changed from ACT to GGT, resulting in the substitution of Glycine for Threonine in the final protein product. In addition, codon number 120, in which GCC codes for Alanine in v-sis, was changed to TAA, a translation termination codon. The resulting protein product of this construction ends with the Arginine at residue 119. Both of the changes were accomplished in one step by insertion of a synthetic DNA fragment after a SmaI site located within codon number 112.

The pUC18/v-sis mutant DNA generated above was restricted with SmaI, which cuts at nucleotide 4324 in the v-sis sequence (numbering system of Devare et al, ibid), and with EcoR1, which cuts in the polylinker of pUC18 just downstream of the v-sis insert. A small fragment (510 base pairs) between the SmaI and EcoR1 sites, coding for the C-terminal portion of the v-sis protein and a 3' untranslated sequence, was removed by electrophoresis on a low-melting temperature agarose gel. The large fragment (about 3530 base pairs) was ligated to a synthetic DNA fragment having the following sequence:

```
5'GGGGGGTTCCCAGGAGCAGCGATAAG      3'
3'CCCCCCAAGGGTCCTCGTCGCTATTCTTAA 5'
```

The GGT codon coding for the new Glycine residue at position 114 and the TAA termination codon introduced at positon 120 are underlined above. This synthetic DNA fragment, shown in FIG. 1, contains a blunt end at its upstream (left) end for ligating to the blunt end created by restriction of the v-sis mutant sequence with Sma$^I$, and an EcoR1 "sticky" end at its downstream (right) end for ligating to the EcoR1 end created by restriction of the pUC18 polylinker with EcoR1. The ligated DNA was transformed into E. coli K12 strain DH5, with transformants being selected by growth on ampicillin-containing medium. The plasmid DNAs from resulting colonies were analyzed for the presence of the synthetic DNA fragment by restriction mapping. Expression of PDGF B$_{119}$ In the final step, the completed form of the mutated v-sis gene was removed from pUC18 and ligated into the E. coli expression vector pCFM1156. The plasmid pCFM1156PL is prepared from the known plasmid pCFM836. The preparation of plasmid pCFM836 is described in U.S. Pat. No. 4,710,473, the relevant portions of the specification, particularly examples 1 to 7, are hereby incorporated by reference. To prepare pCFM1156 from pCFM836, the two endogenous NdeI restriction sites are cut, the exposed ends are filled with T4 polymerase, and the filled ends are blunt-end ligated.

The resulting plasmid is then digested with ClaI and KpnI and the excised DNA fragment is replaced with a DNA oligonucleotide of the following sequence:

```
           ClaI                                                    KpnI
5'CGATTTGATTCTAGAAGGAGGAATAACATATGGTTAACGCGTTGGAATTCGGTAC3'
3'    TAAACTAAGATCTTCCTCCTTATTGTATACCAATTGCGCAACCTTAAGC      5'
```

The pCFM1156 vector contains a region for insertion of foreign genes between an upstream XbaI site and one of a number of downstream restriction sites. In this case, the downstream EcoR1 site was utilized. The pUC18/v-sis mutant DNA generated above was restricted with XbaI and EcoR1, with the small 383 base pair fragment being isolated by electrophoresis on a low-melting temperature agarose gel. This fragment was ligated to pCFM1156 DNA which had also been restricted with XbaI and EcoR1. The ligated DNA was transformed into E. coli K12 strain FM5 (ATCC #67545), with transformants being selected by growth on kanamycin-containing medium. The plasmid DNAs from resulting colonies were analyzed for the presence of the inserted DNA fragment by restriction mapping.

The final expression plasmid contained an inserted DNA sequence which codes for a protein that begins with an initiating methionine, followed by amino acids 1-119 of the human PDGF B chain sequence. The procaryotic E. coli host cells removed the N-terminal methionine after synthesis, so that the final protein produced corresponds to amino acids 1-119 of human PDGF B.

Expression of the 119 amino acid PDGF B protein was confirmed by growing bacterial cells containing the expression plasmid at 28°-30° C. until the desired optical density of the culture was reached, and then shifting the culture to growth at 42° for several hours. Samples of the cultured cells were taken prior to shifting to 42° C., and at several time points thereafter. It was observed, upon SDS-polyacrylamide gel electrophoretic analysis of the bacterial proteins, that a prominent band of apparent molecular weight 14.6 kd was present in temperature-induced, but not preinduced, bacterial cells. This protein was present at an approximate level of 30–40 mg per liter of bacterial culture grown to an optical density at 600 nm of 1.0. Subsequent purification and amino acid sequencing of this protein confirmed that it had the expected sequence for amino acids 1-119 of the human PDGF B chain.

EXAMPLE 2

Refolding of rPDGF B Chain Homodimer from E. coli Inclusion Bodies Using Glutathione as Blocking Agent Approximately 1.5 to 1.6 kg of harvested (i.e., concentrated) E. coli paste from Example 1, containing rPDGF B$_{119}$, was removed for refolding. The E. coli paste was suspended in 9 volumes (v/w) of 20 mM disodium ethylene diamine tetraacetic acid (EDTA), with the temperature being maintained at 4° C. The suspended cell paste was lysed using a Menton-Gaulin homogenizer at a pressure of 14,000 psi and a temperature of 12° C. The lysate was immediately centrifuged at 3,600×G for 60 minutes at 4° C. and the supernatant discarded, with the inclusion body rPDGF-containing pellet being saved.

The pellet was suspended in 14 volumes (v/w) of 8.5M urea, 0.1M glycine, pH 3.0, and stirred for 30 minutes. Meanwhile, SE Sepharose ® (Pharmacia) chromatography resin was drained by placing the commercially available resin in a scintered glass funnel, allowing the resin to drain by gravity, washing the resin with deionized water, and allowing the resin to drain once again. With continued stirring of the resuspended pellet, 2.4 kg of the drained resin was added to the pellet suspension. Stirring was stopped after 30 minutes. The resin was allowed to settle and the supernatant discarded. Five liters of 8.5M urea, 0.1M glycine, pH 3.5, was added to the settled resin. The mixture was stirred for an additional 5 minutes, with the resin again being allowed to settle, and the supernatant being discarded.

Five liters of 8.5M urea, 20 mM phosphoric acid, pH 3.0, were then added to the settled resin. The resulting mixture was again stirred for 5 minutes, with the resin again being allowed to settle, and the supernatant being discarded. A second 5 liter volume of 8.5M urea, 20 mM phosphoric acid, pH 3.0, was added to the settled resin. This mixture, with stirring, was subjected to a vacuum equal to 25 inches of mercury for 30 minutes. The vacuum was then broken, and the mixture was made 5 mM in dithiothreitol (DTT), with the pH being adjusted to 7.7 with 10M sodium hydroxide (NaOH). The vacuum was restored and the mixture stirred for 30 minutes. Still under vacuum, with stirring discontinued, the resin was allowed to settle and 90% of the supernatant discarded.

The resin was immediately slurried with the residual liquid and poured into a 25 cm diameter column (batch column), the flow adapter attached, and the resin packed at 100 cm/hour for 10 minutes with 8.5M urea, 20 mM sodium phosphate ($Na_2HPO_4$), pH 7.7 that had been and was being sparged with $N_2$ gas (buffer A). The flow adapter was lowered to the surface of resin and the column washed with additional buffer A at a flow rate of 25 cm/hour until the effluent absorbance at 280 nm was constant.

The outlet of the batch column was then connected to the inlet of a second 25 cm×20 cm column (resolving column) packed with fresh SE Sepharose® (Pharmacia) and equilibrated with buffer A. The batch and resolving columns were then resolved at a flow rate of 25 cm/hour with an 80-liter linear gradient from 100% buffer A to 100% buffer B (8.5M urea, 20 mM $Na_2HPO_4$, 0.4M NaCl, pH 7.7) which had been and was being sparged with $N_2$ gas. The appropriate fractions were immediately pooled and placed under vacuum as they came off the column. Yield was between 0.45 and 0.90 gm per liter of fermentation broth.

The denatured monomeric rPDGF B119-containing solution was diluted, if necessary, to an absorbance of between 0.4 and 0.50.D. The protein solution was then made 0.1M in oxidized glutathione and the pH adjusted to 8.0 with 10M NaOH. The solution was again placed under vacuum and stirred for 18 to 24 hours. The vacuum was broken and the pH of the now derivatized monomeric rPDGF mixed disulfide intermediate was lowered to 3.0 with HCl. The resultant solution was concentrated to ½ the initial volume, and then diafiltered first against four volumes of 8.5M urea, 0.1M acetic acid, and then followed by four volumes of 0.1M acetic acid using an Amicon YM® 10 (Amicon Inc., Danvets, Mass.) ultrafiltration membrane. The final protein concentration was between 1.5 and 2.0 mg/mL $\epsilon_{280nm}^{1\%}=0.46$) with rPDGF-S—S—G monomer purity >85%, and yield of between 0.45 and 0.90 gm per liter of fermentation broth.

Refolding was effected by dilution of the rPDGF-S-S-G solution to 0.1 mg/mL with 20 mM Tris. Subsequently, 1M cysteine in 0.1M acetic acid was added to this solution, to a final concentration of 1 mM, and the pH adjusted to 8.0 with NaOH. The solution was allowed to stir for 16 hours, in order to unblock the derivatized rPDGF-S—S—G monomeric intermediate and initiate formation of intrachain and interchain disulfide bonds, and then made 0.1M in acetic acid. Yield was 0.32 to 0.63 gm per liter of fermentation broth.

The refolded rPDGF dimer solution was loaded, at a flow rate of 100 cm/hr, onto a 11.3×5 cm column of controlled pore glass (CPG, pg-350–400, 96M²/gm, 382 Å mean pore diameter, Sigma Chemical Company, St. Louis, Mo.), equilibrated in either 0.05M glycine, pH 3.5 (buffer C) or 0.05M glycine, 0.4M NaCl, pH 3.5 (buffer D). Following the loading of the PDGF postoxidation solution onto the column, the column was washed with the equilibration buffer at a flow rate of 40 cm/hr. The purified PDGF dimer was then eluted from the column, again at a flow rate of 40 cm/hr, by the application of a 5 liter gradient starting with either buffer C or D and finishing with either 2M guanidine.HCl in buffer C or 8M urea in buffer D.

The appropriate fractions of pure PDGF were pooled. The yield was between 0.25 and 0.5 gm per liter of fermentation broth.

EXAMPLE 3

Mitogenic Activity of Refolded rPDGF B Chain Homodimer

The refolded rPDGF $B_{119}$ homodimer from Example 2 was assayed for mitogenic activity by a thymidine uptake assay using normal rat kidney cells, Clone 49F, ATCC #CRL-1570 (NRK) by a modification of the method described by Pierce et al, *J. Exp. Med.*, 176, 974–987 (1988), using mammalian dimeric rPDGF B from CHO cells as a standard. The NRK cells were grown in a growth medium (FBS-DMEM) comprising: (1) Dulbecco's Modified Eagle Medium (DMEM), containing 1 g/L glucose, 1% (w/v) penicillin-streptomycin solution (100×, 10,00 units penicillin, 10,000 μg streptomycin/mL), and 1% (v/v) L-glutamine solution at 100×, 200 mM; and, (2) 7.5% Fetal Bovine Serum (FBS) (Whitaker MA Bioproducts, Walkersville, Md.).

Cells were plated into 24-well microtiter plates at a density of 2×10⁴ cells/well in FBS-DMEM. After 5 days, the FBS-DMEM was aspirated and replaced with 1 mL of DMEM without FBS, in order to "starve" the cells so that they might respond more markedly upon exposure to PDGF. The cells were incubated in this medium for 24 hours, after which time, 50 μL of a PDGF-containing sample was added to each well. After a further 18 hour incubation, the PDGF-containing sample was aspirated and replaced with 1 mL of labeling medium consisting of DMEM, 5% FBS, and 2 μCi/mL of ³H-thymidine. The plates were incubated for an additional 1 hour at 37° C. Cells from triplicate wells were detached with a sucrose/EDTA solution and harvested with an automated microharvester onto glass fiber filter mats. The cells were fixed onto the mats with ethanol, and after drying, the mats were counted in a scintillation counter.

The average value of control wells receiving no PDGF was subtracted from the averaged triplicate counts of each experimental sample. The log of the PDGF concentration in ng/mL was plotted vs. cpm incorporated for each sample. The results are set forth in FIG. 2. These results demonstrate that the refolded rPDGF $B_{119}$ homodimer from Example 2 has substantially the same mitogenic activity as the dimeric rPDGF B from the eucaryotic CHO host cells.

EXAMPLE 4

Chemotactic Activity of Refolded rPDGF b Chain Homodimer

The refolded rPDGF $B_{119}$ homodimer from example 2 was also assayed for chemotactic activity on fibroblasts and monocytes essentially as described in Senior et al, *J. Cell. Biol.*, 96, 382–385 (1983); Deuel et al, *J. Clin. Invest.*, 69, 1046–1049 (1982). The rPDGF $B_{119}$ homodimer from Example 2 was tested in Boyden chambers as described in the referenced articles, using mammalian dimeric rPDGF B from CHO cells as a standard. In this test, cells migrate through a filter, from one chamber without a chemotactic agent to another chamber with a chemotactic agent. After a given period of time, the number of cells in a microscopic field on the side with the chemoattractant are counted.

Fibroblasts were obtained from explants of normal adult skin surgical specimens. The cells were cultured in Dulbecco's modified Eagle's medium (DMEM), supplemented with 2 mM L-glutamine, nonessential amino acids, and 10% fetal bovine serum (KC Biological, Inc., Lenexa, Kans.). The cells were used for assays after six passages. Human blood mononuclear cells (monocytes) were obtained using Ficoll/Hypaque gradients, and suspended in DMEM supplemented with 2% human albumin at densities of $2.5 \times 10^6$ cells/mL.

Chemotaxis was determined in a multi-blind well apparatus having 30 wells. A double-membrane technique, using a polycarbonate membrane (Nucleopore Corporation, Pleasanton, Calif.) with 8 μm pores (fibroblasts) or 5μm pores (monocytes) on top of a cellulose nitrate membrane (Millipore Corporation, Bedford, Mass.) having 0.45-μm pores, was used to separate each well into an upper and lower compartment. The lower compartment was filled with either PDGF solution to be assayed, or control medium, then covered with the membranes, in the appropriate order, after which a cell suspension containing fibroblasts or monocytes was added to the upper compartment. After both compartments of the wells were filled, the chemotaxis apparatus was placed in a humidified incubator at 37° C. in an atmosphere of 5% carbon dioxide/95% air for 6 hours. The apparatus was then disassembled and each membrane pair was removed and stained.

Figure 3:
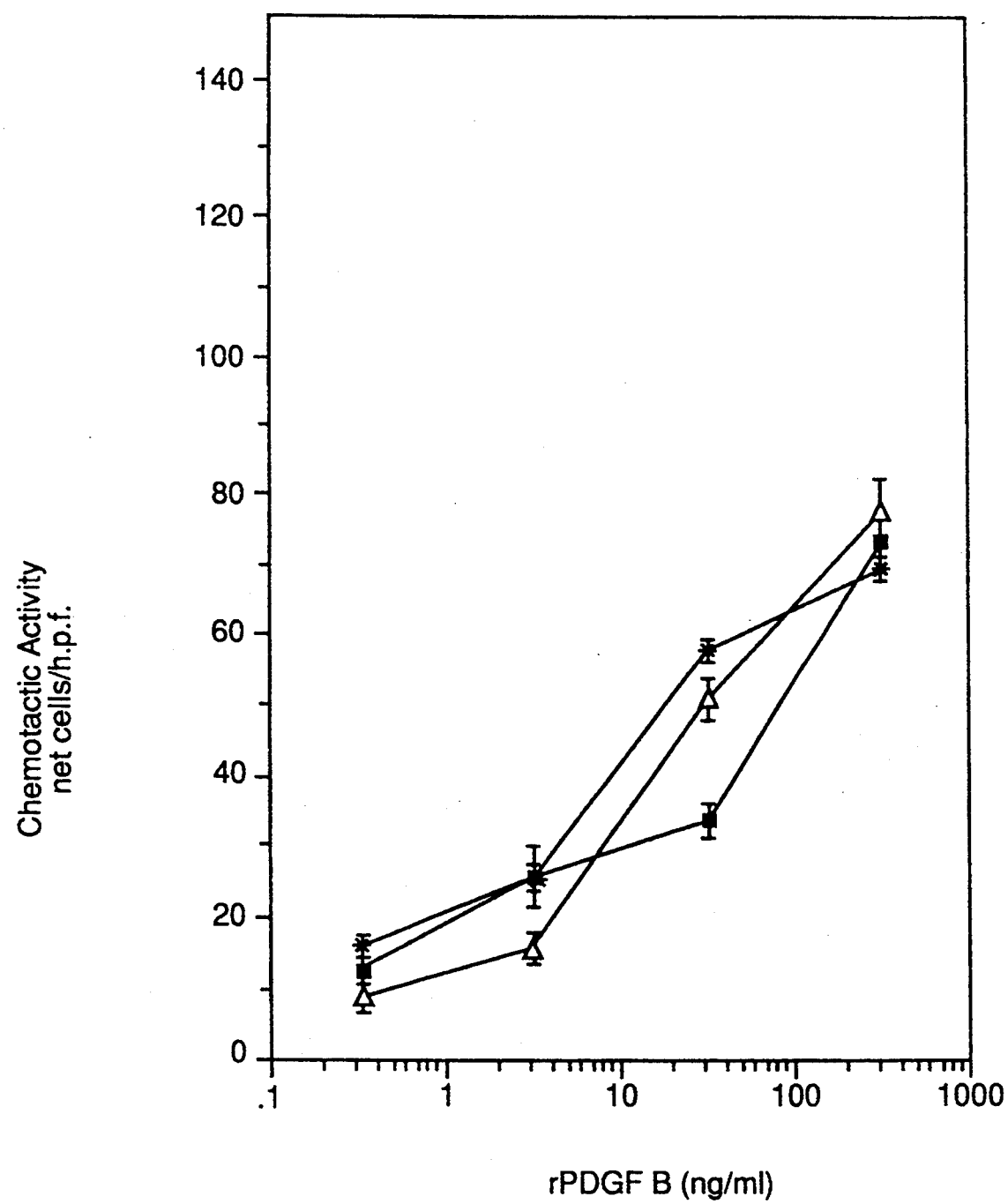
FIG. 3 is a graph showing the chemotactic activity on fibroblasts of *E. coli*-produced rPDGF $B_{119}$ which has been refolded in accordance with the teachings of the present invention.
Figure 4:
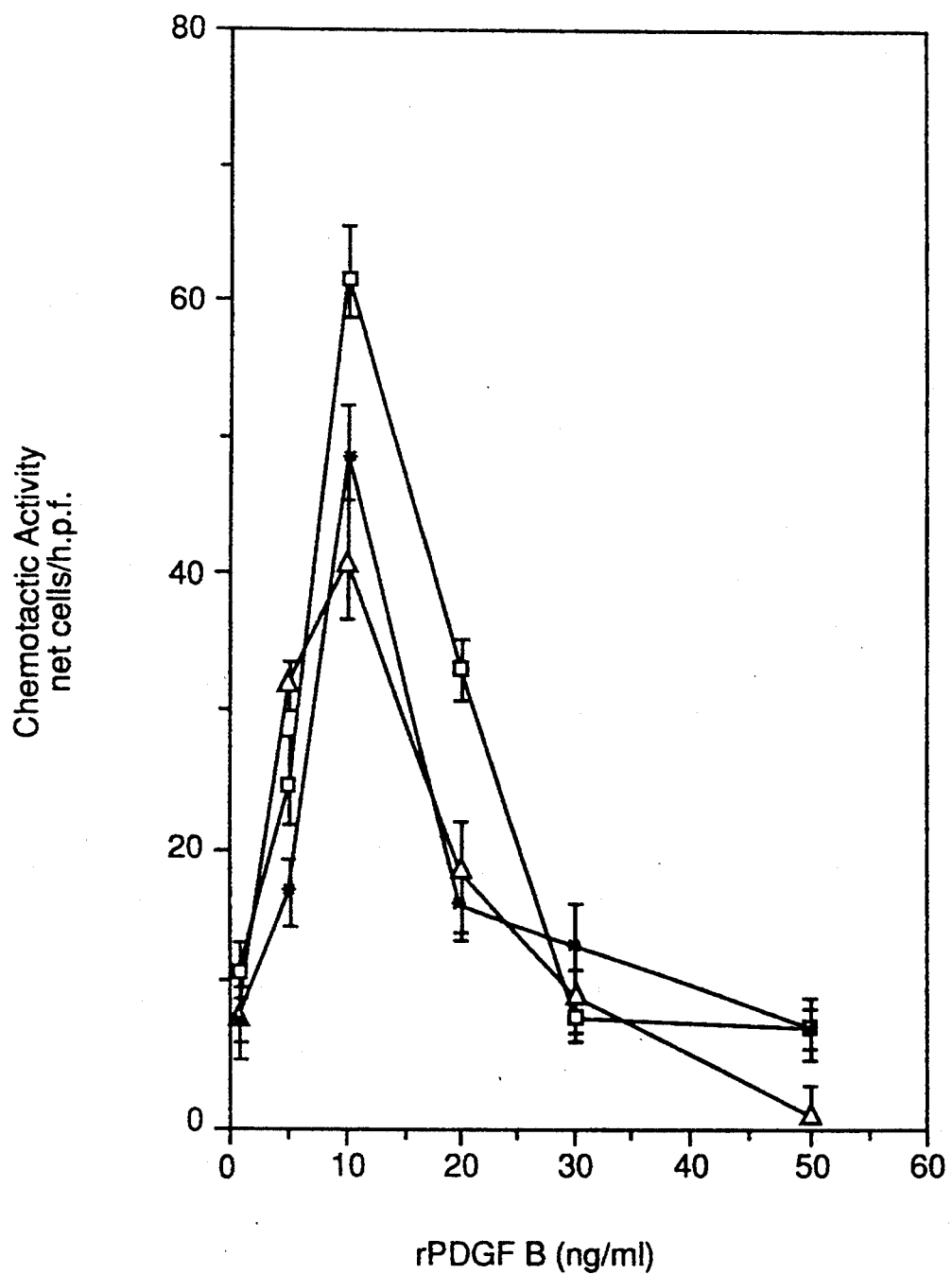
FIG. 4 is a graph showing the chemotactic activity on monocytes of *E. coli*-produced rPDGF $B_{119}$ which has been refolded in accordance with the teachings of the present invention.

Cell migration was determined by counting, under high-power magnification ($\times 400$), the cells that had moved to the interface between the two membranes and those on the lower membrane. Five high-power fields (hpf) were counted per membrane pair. Cell migration is expressed as the net number of cells migrated per hpf, that is, the number of cells per hpf minus the number of cells per hpf that migrated in response to control medium. The results from the chemotaxis assay on fibroblasts is shown in FIG. 3 and on monocytes in FIG. 4. These results show the refolded rPDGF $B_{119}$ homodimer from Example 2 to have substantially the same chemotactic activity as the dimeric rPDGF B from the eucaryotic CHO host cells.

EXAMPLE 5

Production of rPDGF A

There are at least two forms of naturally occurring PDGF A, with slight amino acid sequence variations. The long form, PDGF $A_L$, also known as glioma PDGF A, is 125 amino acids in length. The short form, PDGF $A_S$, also known as endothelial PDGF A, is 110 amino acids long. Any form of PDGF A, or analog(s) thereof, can be refolded using the method of the present invention. However, PDGF $A_L$ was selected for demonstration of the refolded method disclosed herein, and was synthesized according to the coding sequence shown in FIG. 5. Specifically, the coding sequence for PDGF $A_L$ was synthesized using a four-step procedure with several intermediate washes, as set forth below. Syntheses were performed on an Applied Biosystems, Inc. (Foster City, Calif.) Model 380 automated synthesizer using commercially available reagents.

Polymer-bound dimethoxyltrityl-protected nucleoside (first nucleic acid in sequence) in support columns was first stripped of its 5' dimethoxytrityl protecting group by passing a solution of 3% trichloroacetic acid in dichloromethane through the column for one minute. The polymer was then washed with acetonitrile, followed by rinsing with dry acetonitrile. The polymer, containing the deprotected nucleoside, was then placed under argon prior to proceeding to the next (condensation) step.

The condensation step was carried out by first treating the polymer with tetrazole in acetonitrile. The polymer-bound deprotected nucleoside was then reacted with a protected cyanoethyl nucleoside phosphoramidite (second nucleic acid in sequence; Applied Biosystems, Inc.) in acetonitrile. The condensation reaction was allowed to proceed for 2.0 minutes, with the reactants being subsequently removed by filtration.

Condensation was followed by capping the unreacted 5'-hydroxyl groups of the nucleosides by passing a solution prepared by mixing one part of a mixture available from Applied Biosystems, Inc., containing acetic anhydride and 2,6-lutidine in THF (tetrahydrofuran), and one part 1-methylimidazole in THF (also available from Applied Biosystems, Inc.) through the column for one minute.

Following removal of the capping solution, the polymer was treated for 1.5 minutes with an oxidizing solution (0.1M $I_2$ in $H_2O$/2,6-lutidine/THF, 1:10:40). This was followed by an acetonitrile rinse. The cycle began again with a trichloroacetic acid/methylene chloride deprotection and was repeated until the desired PDGF $A_L$ coding sequence was obtained.

The polymer-bound PDGF $A_L$ coding sequence was treated with fresh concentrated ammonia at room temperature for 2.0 hours. After decanting the solution from the polymer, the concentrated ammonia solution was heated at 60° C. for 16 hours in a sealed tube.

The solution containing the PDGF $A_L$ coding sequence was extracted with 1-butanol and ethyl ether, with the concentration of the extracted solution being determined spectrophometrically by measuring absorption at 260 nm. An aliquot of the extracted solution containing 5.0 O.D. units of synthesized oligonucleotide was concentrated for preparative electrophoresis and loaded into a 15% polyacrylamide 7M urea gel. After electrophoresis, the product band was visualized by U.V. shadowing, cut from the gel, extracted with elution buffer (300 mM sodium acetate (NaOAc) 2.5 mM EDTA, 100 mM Tris-HCl, pH 8.0), and then desalted on a G-50 Sephadex ® (Pharmacia LKB Biotech, Inc., Piscataway, N.J.) column using TEAB eluant (triethyl ammonium bicarbonate) to yield the purified oligonucleotide.

Expression of PDGF A

The completed form of the PDGF $A_L$ coding sequence was ligated into the *E. coli* expression vector pCFM1156. In this case, the upstream NdeI site and the downstream BamH1 site were utilized. The earlier described pCFM1156 DNA was restricted with NdeI and BamH1, and the large vector fragment was ligated with the synthetic PDGF $A_L$ gene, which contained "sticky" NdeI and BamH1 ends. The ligated DNA was transformed into *E. coli* K12 strain FM5 (ATCC #67545), with transformants being selected by growth on kanamycin-containing medium. The plasmid DNAs from resulting colonies were analyzed for the presence of the inserted DNA fragment by restriction mapping.

The final expression plasmid contained an inserted DNA sequence which codes for the human PDGF $A_L$ chain sequence. The bacterial cells remove the N-terminal methionine after synthesis, so that the final protein produced corresponds to the 125 amino acid long human form of PDGF $A_L$.

Expression of the PDGF $A_L$ protein was confirmed as described for PDGF $B_{119}$ in Example 1. It was observed, upon SDS-polyacrylamide gel electrophoretic analysis of the bacterial proteins, that a prominent band of apparent molecular weight 18 kd was present in heat-induced, but not pre-induced, bacterial cells. This protein was present at an approximate level of 25 mg per liter of bacterial culture grown to an optical density at 600 nm of 1.0. Subsequent purification and amino acid sequencing of this protein confirmed that it had the expected sequence for the human PDGF $A_L$ chain.

EXAMPLE 6

Refolding of rPDGF $A_L$ Chain Homodimer from *E. coli* Inclusion Bodies Using Glutathione as Blocking Agent The rPDGF $A_L$ from Example 5 was refolded into a biologically active homodimer in the same manner as set forth in Example 2, with the exception that the actual refolding step was effected by the dilution of the rPDGF-S—S—G monomer solution to 0.05 mg/mL, with 20 mM Tris. Subsequently, 1M cysteine in 0.1M acetic acid was added to this solution, to a final concentration of 1 mM, and the pH adjusted to 7.5, with NaOH. The solution was allowed to stir for 16 hours and then made 0.1M in acetic acid. Yield was 0.19 to 0.38 gm per liter of fermentation broth.

The refolded rPDGF dimer solution was loaded, at a flow rate of 100 cm/hr, onto a 10.0×5 cm column of controlled pore glass (CPG pg-350–400, 96M$^2$/gm, 382 Å mean pore diameter, Sigma Chemical Company, St. Louis, Mo.), equilibrated in either 0.05M glycine, pH 3.5 (buffer C), or 0.05M glycine, 0.4M NaCl, pH 3.5 (buffer D). Following the loading of the PDGF post-oxidation solution onto the column, the column was washed with the equilibration buffer at a flow rate of 40 cm/hr. The purified PDGF dimer was eluted from the column, again at a flow rate of 40 cm/hr, by the application of a 4 L linear gradient starting with either buffer C or D and finishing with either 2M guanidine.HCl in buffer C or 8M urea in buffer D.

The appropriate fractions of pure PDGF dimer were pooled. The yield was between 0.15 and 0.3 gm per liter of fermentation broth.

EXAMPLE 7

Mitogenic Activity of Refolded rPDGF A Chain Homodimer

Figure 6:
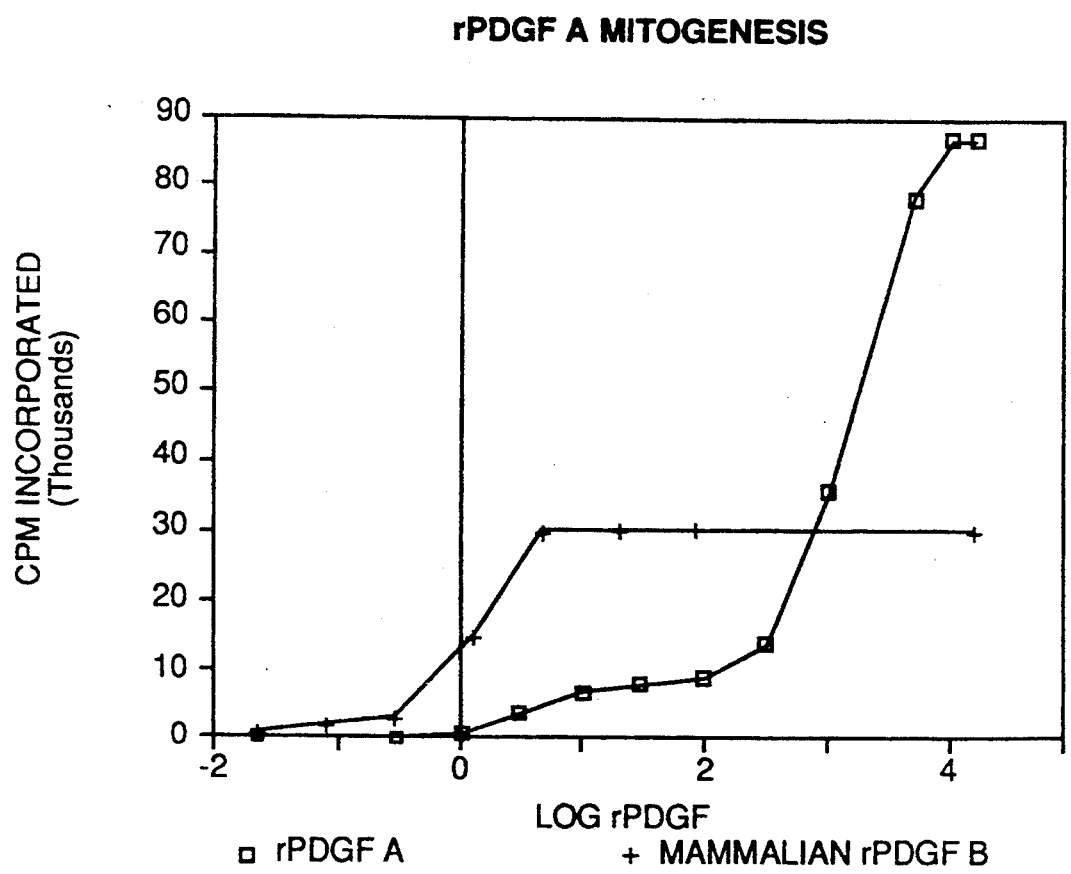
FIG. 6 is a graph showing the mitogenic activity of *E. coli*-produced rPDGF $A_L$ which has been refolded in accordance with the teachings of the present invention.

The mitogenesis assay was carried out as set forth in Example 3. At lower concentrations, and in the absence of other growth factors, the activity of PDGF A homodimer on NRK cells is considerably less than that of PDGF B homodimer. The results are set forth in FIG. 6.

EXAMPLE 8

Refolding of rPDGF A-B Chain Heterodimer from *E. coli* Inclusion Bodies Using Glutathione as Blocking Agent Recombinant PDGF A-B heterodimer was refolded in the same manner as set forth in Example 6, with the exception that ⅔ of the total protein at 0.1 mg/mL was provided by rPDGF $B_{119}$-S—S—G monomer, with the remaining ⅓ of the total protein being provided by rPDGF AL-S—S—G monomer. These relative concentrations were selected to favor formation of the heterodimer by discouraging formation of the rPDGF A-A homodimer. Chromatography of the refolded PDGF A-B heterodimer was performed by immobilized metal ion affinity chromatography (IMAC) and by reverse phase HPLC, essentially followed procedures reported by A. Hammacher et al, *J. Biol. Chem.*, 263, 16493–16498.

The refolded rPDGF dimer solution was first chromatographed on controlled pore glass as set forth in Example 6, with the appropriate fractions being pooled, and the pooled refolded rPDGF then being diafiltered against 0.1M acetic acid behind an Amicon 10K membrane. The pH of the pooled PDGF was adjusted to 7.4 with NaOH, and then loaded on a 2.6×10 cm Chelating Sepharose ® (Pharmacia) column charged with Cu++ ion equilibrated with 20 mM Na$_x$PO$_4$, 1 mM imidazole, 1M NaCl, pH 7.4 (buffer A). The column was then resolved with a 1 liter linear gradient between buffer A and 20 mM Na$_x$PO$_4$, 10 mM imidazole, 0.7M NaCl, pH 7.4 (buffer B). The appropriate fractions were then pooled.

Figure 7:
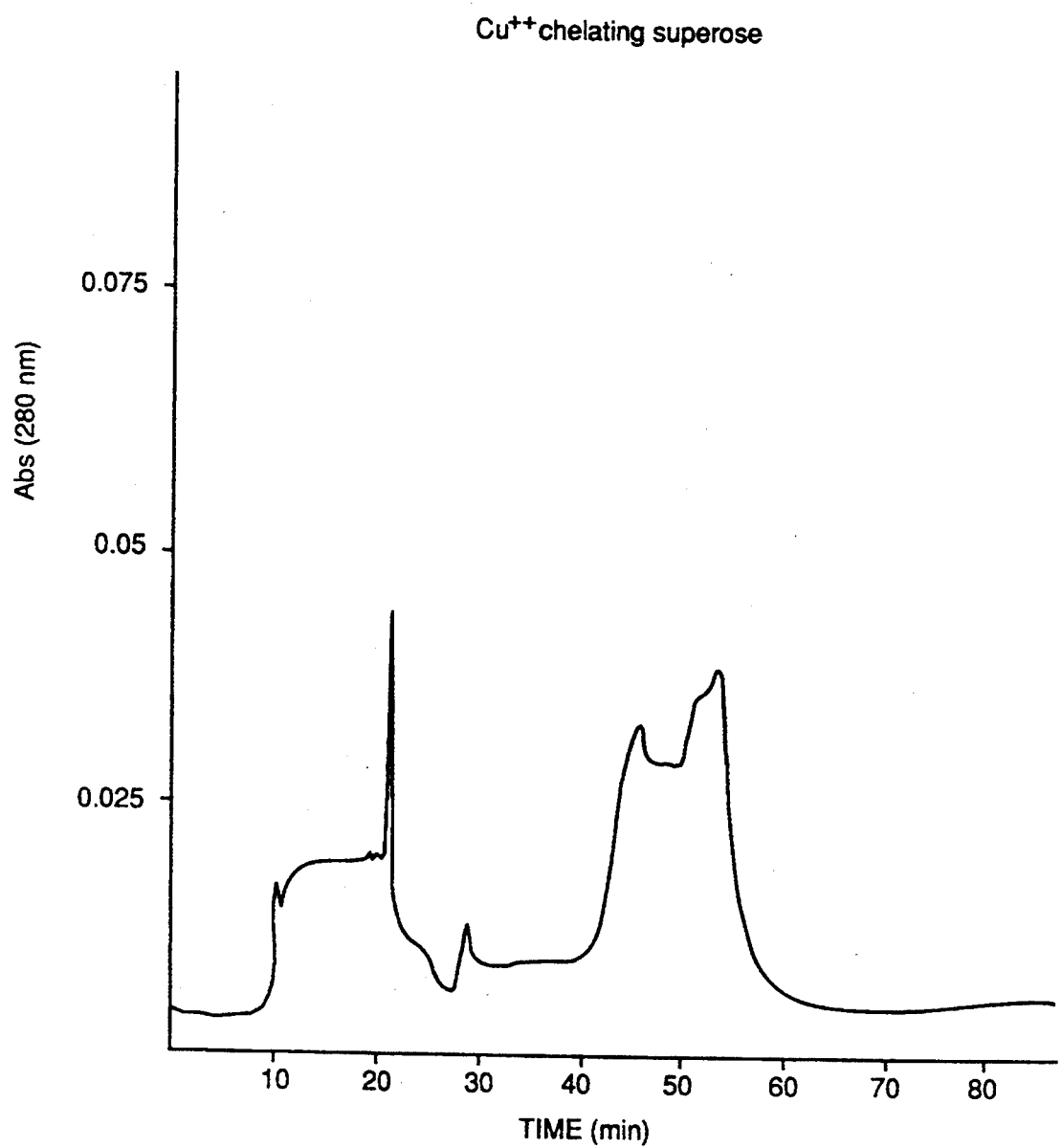
FIG. 7 is a graph showing the chromatographic separation of purified pooled fractions of rPDGF A-B heterodimer solution refolded according to the present invention.
Figure 8A:
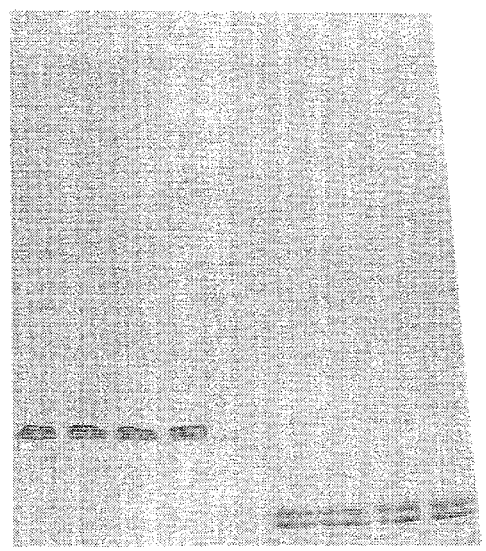
FIG. 8A shows the reproduction of a Coomassie Brilliant Blue stained SDS-PAGE gel, of samples taken across the peaks of the refolded rPDGF A-B heterodimer solution shown in FIG. 7.
Figure 8B:
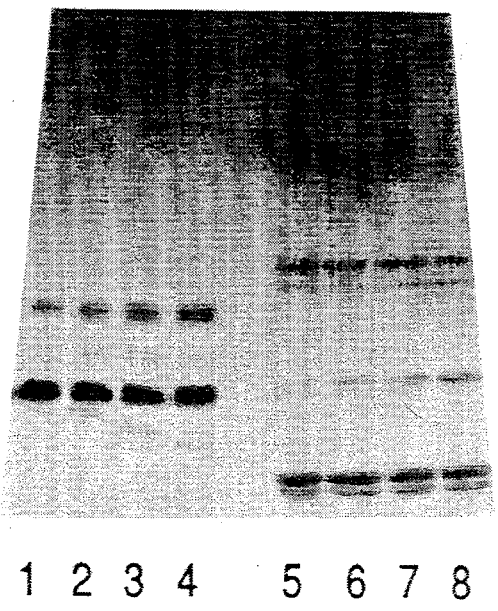
FIG. 8B is a reproduction of the SDS-PAGE gel from FIG. 8A which has been silver stained.

The pooled fractions were brought up to 25 mM in disodium phosphate and 1 mM imidazole prior to filtration through a 1.6 mL Cu$^{2+}$-chelating Superose ® (Pharmacia) column equilibrated with 1 mM imidazole/1M NaCl/20 mM NaPO$_4$, pH 7.5 (Buffer A). Under these conditions, PDGF B homodimer does not bind. The column was then washed with 95% Buffer A and 5% Buffer B (30 mM imidazole/0.7M NaCl/20 mM NaPO$_4$, pH 7.5), followed by a linear gradient to 405 in Buffer B. Multiple overlapping components were evident, as shown in FIG. 7. SDS-PAGE analysis of samples across the peaks gave identical patterns which, on reduction, yielded two bands of comparable intensities after Coomassie blue staining (FIG. 8A). The gel was subsequently silver stained and a reproduction of that gel is shown in FIG. 8B.

The leading and trailing peaks from the Cu$^{2+}$-chelating Superose ® (Pharmacia) column were examined independently by HPLC on a Vydac C4 column using a 2-propanol gradient in 2M guanidine-hydrochloride, 1M acetic acid.

Figure 9:
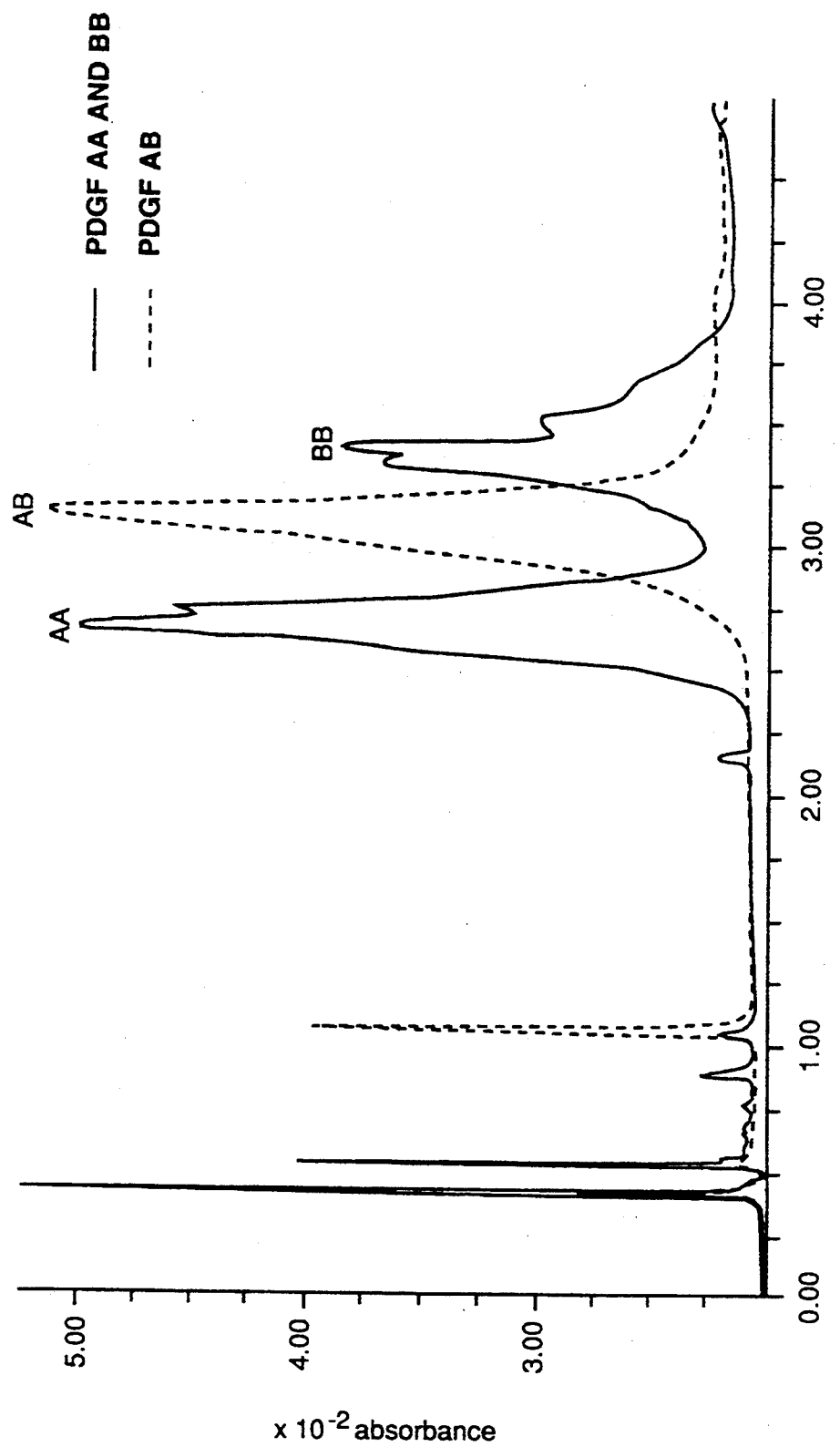
FIG. 9 demonstrates the retention time of the refolded rPDGF A-B heterodimer from one of the pooled fractions of Example 8 relative to the retentions times for rPDGF $B_{119}$ and rPDGF $A_L$ homodimer.

The retention times for the various polypeptides are given in Table I, below. The HPLC profile of one of the fractions from the Cu$^{2+}$-chelating column relative to PDGF A homodimer, which elutes earlier, and PDGF B homodimer, which elutes later, is set forth in FIG. 9.

TABLE I

| Retention Times for Various Forms of rPDGF | |
|---|---|
| rPDGF | R$_T$ (minutes) |
| rPDGF A$_L$-S-S-G | 27.5–27.9 |
| rPDGF B-S-S-G | 41.8 |
| rPDGF A-A homodimer | 26.5–27.2 |
| rPDGF B-B homodimer | 33.9–35.0 |

From the results presented herein, both fractions from the Cu$^{2+}$-chelating column represent A-B heterodimers of PDGF. The leading fraction from this column had an absorbance maximum at 268 nm, whereas the trailing peak had an absorbance maximum at 280 nm (FIGS. 10A and 10B).

EXAMPLE 9

Production of a PDGF $B_{109}$ Analog With Altered Cysteine Residues

A PDGF $B_{109}$ [Ser$^{43}$,Ser$^{52}$,Ser$^{53}$,Ser$^{99}$] analog was designed for the production of an unblocked biologically active monomer, according to the method of the present invention. The cysteine residues at amino acid positions 43, 52, 53, and 99 were identified for substitution with serine residues on the basis of a previous study by Giese et al suggesting that the corresponding residues in the v-sis gene may not be required for dimerization of the v-sis molecule. Giese et al, *Science*, 236, 13–15 (1987). Alteration of the corresponding cysteine residues in v-sis was reported to disrupt dimerization, but not the transforming activity of v-sis. Giese et al, ibid.

A gene for *E. coli* expression of the PDGF $B_{109}$ [$Ser^{43}, Ser^{52}, Ser^{53}, Ser^{99}$] analog shown in FIG. 10, was constructed using strategies similar to those described for constructing the PDGF $B_{119}$ form, as set forth in Example 1. In the case of the analog, the gene was designed to express a 109 amino acid form of PDGF B. The starting material was the same v-sis gene used in Example 1, with the four amino acid differences between the v-sis prtoein and human PDGF B (i.e., residues 6, 7, 100, and 107) being changed to the human form of PDGF B as set forth in Example 1. These changes involved the in vitro mutagenesis of amino acids 100 and 107, and replacement of the 5'-end of the gene with a synthetic DNA fragment changing amino acids 6 and 7. The synthetic DNA fragment also provided a translation initiating ATG codon preceding the Serine 1 codon, as well as an upstream XbaI site for ligation into the desired *E. coli* expression vector.

The resulting DNA was used as a template for further mutagenesis reactions to introduce four cysteine to serine changes and a stop codon at position 110. As earlier noted, the four cysteine residues which were changed are those residues at amino acid positions 43, 52, 53, and 99. Four oligonucleotides were employed to effect these changes. Oligonucleotide 1, having the sequence:

3' CACCGGCGGGAGGCACCTCCA 5', was used to mutate Cysteine 43. Oligonucleotide 2, having the sequence:

3' CGCGACGAGGCCGAGAAGGTTGTTGGCGTTGC 5', was used to mutate Cysteine 52 and Cysteine 53. Oligonucleotide 3, having the sequence:

3' CGTACGTTCAGACTCTGTCAC 5', was used to mutate Cysteine 99, and oligonucleotide 4, having the sequence:

3' GGACACTGGACTTCGGGCC 5', was used to mutate the codon for Arginine 110 to the stop codon TGA. The underlined nucleotides denote the changes from the v-sis to the human PDGF B sequence. The in vitro mutagenesis was performed as described for construction of the PDGF $B_{119}$ gene, except that all four oligonucleotides were mixed, and the five mutations were introduced together in one reaction. Also, instead of nicking the non-mutant strands with the enzyme NciI, the alternate enzyme PvuI was used, because oligonucleotide 4 (noted above) contains an NciI recognition site. A resulting M13mp18/PDGF B plaque was isolated, the DNA purified, and sequenced. The DNA sequence showed that all of the desired mutations had been introduced as expected.

Double-stranded M13mp18/PDGF B RF DNA was prepared from this phage and restricted with SalI and SmaI. SalI cuts upstream of the PDGF B sequence, and SmaI cuts in the PDGF sequence at a location five nucleotides downstream from the stop codon introduced at position 110. This fragment was ligated into the vector pUC18, which had also been restricted with SalI and SmaI. This step resulted in a deletion of the large 3' untranslated region of v-sis between the SmaI and downstream XbaI sites.

The mutant PDGF B gene, containing the desired four cysteine to serine changes and stop codon following Threonine 109, was removed from pUC18 by restriction with XbaI and EcoR1. (There is an EcoR1 site in pUC18 just downstream of the SmaI site.) This fragment was ligated into the *E. coli* strain FM 5 (ATCC No. 53911), and resulting recombinant colonies were selected. One of the selected colonies was further analyzed as described below.

The transformed host cell FM5/pCFM1156/PDGF $B_{109}$ [$Ser^{43}, Ser^{52}, Ser^{53}, Ser^{99}$] was shown to produce PDGF B proteins, using methods similar to those described in Example 1. SDS-PAGE revealed two closely-spaced bands, indicating the presence of two proteins. The lower band corresponds to the expected 109 amino acid form of PDGF $B_{109}$ [$Ser^{43}, Ser^{52}, Ser^{53}, Ser^{99}$] analog, while the higher band corresponds to a 129 amino acid PDGF B "readthrough" product which contains an additional twenty amino acids at its carboxy terminus. These additional amino acids are derived from pUC18 and from the vector pCFM1156. This "readthrough" product stops translation at a stop codon present in the pCFM1156 vector.

Following purification, as described in Example 1, the reduced monomeric PDGF $B_{109}$ [$Ser^{43}, Ser^{52}, Ser^{53}, Ser^{99}$] from the cell paste was then refolded in the same manner as the PDGF $B_{119}$ homodimer, as set forth in Example 2. In the case of the PDGF $B_{109}$ [$Ser^{43}, Ser^{52}, Ser^{53}, Ser^{99}$] analog, refolding resulted in a PDGF B monomer, rather than the dimeric form of PDGF $B_{119}$ from Example 2.

EXAMPLE 10

Comparative Mitogenic Activities of Refolded PDGF $B_{119}$ Homodimer, PDGF $B_{109}$ Analog Monomer, and PDGF $B_{119}$ and PDGF $A_L$ Mixed Disulfide Monomeric Intermediates The PDGF $B_{109}$ [$Ser^{43}, Ser^{52}, Ser^{53}, Ser^{99}$] analog monomer from Example 10, the blocked monomeric PDGF $B_{119}$ intermediate from Example 2, and the blocked monomeric PDGF $A_L$ intermediate from Example 6 were assayed for mitogenic activity, as set forth in Example 3. The PDGF $B_{119}$ homodimer from Example 2 was used as a standard. Suprisingly, all three of the monomeric forms of PDGF exhibited mitogenic activity, although it took much more monomer than dimer (500 to 1,000 times as much) to achieve the same maximal activity achievable with the PDGF $B_{119}$ homodimer used as a standard. Even more surprisingly, the maximal activity that could be achieved with all three of the tested monomers was 3 to 3.5 times higher than could be achieved with any quantity of the PDGF $B_{119}$ homodimer.

In the following assays, the above-identified three monomers and PDGF $B_{119}$ homodimer are designated as set forth in the following table.

TABLE II

| Identification of Monomers and Dimers | |
|---|---|
| rPDGF $A_L$-S-S-G | mA-g |
| rPDGF $B_{119}$-S-S-G | mB-g |
| rPDGF $B_{analog}$-S-S-G | mB(4cys)-g |

TABLE II-continued

| Identification of Monomers and Dimers | |
| --- | --- |
| rPDGF B$_{analog}$ | mB(4cys)-f |
| rPDGF B$_{119}$ homodimer | BB or PDGF-BB |

Mitogenic Activity of Derivatized PDGF Monomers

The monomers mB-g and mA-g were assayed for mitogenic activity on NRK cells, as set forth in Example 3, using the control PDGF B$_{119}$ homodimer (BB) as a standard. The results are shown in FIG. 11. While the maximal achievable activity of the dimer is seen to peak at about 30 cpm×10$^{-3}$ (after reaching a concentration of about 4 ng/ml), the monomers required 300–1000 ng/ml to achieve comparable activity. At even higher concentrations, however, the activity of the monomers far exceeds the maximum observed for the dimer.

Mitogenic Activity of PDGF B$_{109}$ Analog Monomer

Figure 12:
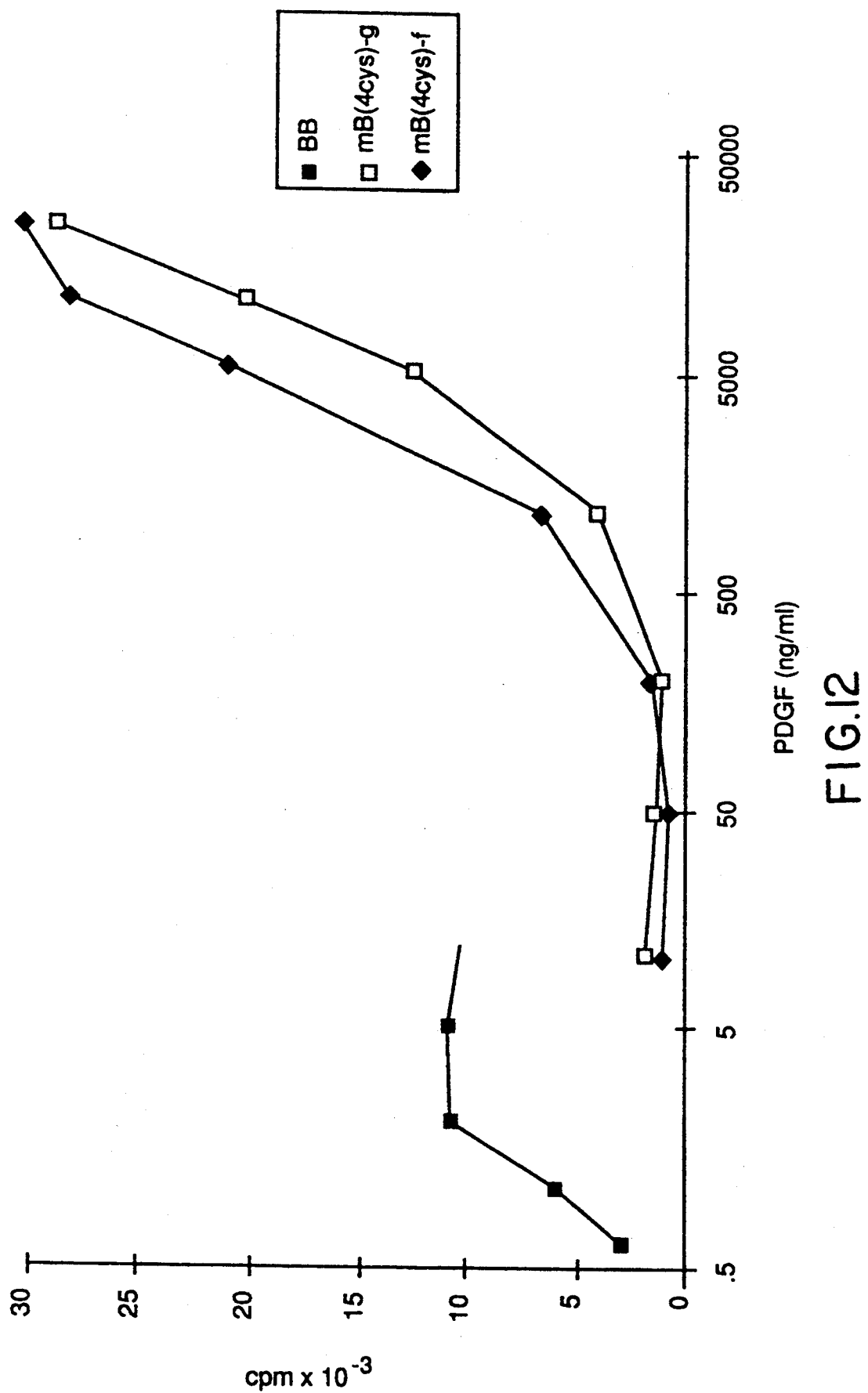
FIG. 12 demonstrates the activity of the monomeric mixed disulfide intermediate of PDGF $B_{109}$ [$Ser^{43}$,$Ser^{52}$,$Ser^{53}$,$Ser^{99}$] analog and the unblocked PDGF $B_{109}$ [$Ser^{43}$,$Ser^{52}$,$Ser^{53}$,$Ser^{99}$] analog, as compared with PDGF $B_{119}$ homodimer.

Both the derivatized mixed disulfide intermediate (mB(4cys)-g) and unblocked (mB(4cys)-f) versions of the PDGF B$_{109}$ [Ser$^{43}$,Ser$^{52}$,Ser$^{53}$,Ser$^{99}$] analog were assayed for mitogenic activity, as set forth in Example 3, using the control PDGF B$_{119}$ homodimer (BB) as standard. The results are shown in FIG. 12. Similar results were obtained as those observed with respect to the derivatized monomers mA-g and mB-g.

EXAMPLE 11

Verification of Monomeric forms of rPDGF

In order to verify that the activities observed in Example 11 were indeed the result of the presence of monomeric forms of rPDGF (i.e., rather than the presence of contamination of the sample with some degree of residual dimeric form), the following analyses were performed.

SDS-PAGE Analysis

SDS-PAGE analysis of mB(4cys)-g and mB(4cys)-f was performed to analyze the molecular weight composition of these monomer samples. Each of the two monomer proteins was electrophoresed on a 12% SDS-polyacrylamide gel, using sample sizes of both 0.25 and 0.5 µg for each monomer. Neither monomer sample was treated with the reducing agent 2-mercaptoethanol prior to being subjected to electrophoresis. Molecular weight standards were run in parallel, and the resulting gel silver-stained. No presence of dimer was observed.

Differential Sensitivity to Identified Agents

The monomeric and dimeric forms of PDGF are also expected to exhibit different sensitivities to various agents when contacted with these agents. In the first instance, mB(4cys)-g, mB(4cys)-f, and PDGF-BB were exposed to heat, SDS, and mildly reducing conditions, with the resulting effects on the relative activities of these proteins being compared. In the second instance, the relative activities of the same PDGF forms were compared following exposure to SDS and strongly reducing conditions.

A. Effects of Heat, SDS, and Mildly Reducing Conditions

Figure 13:
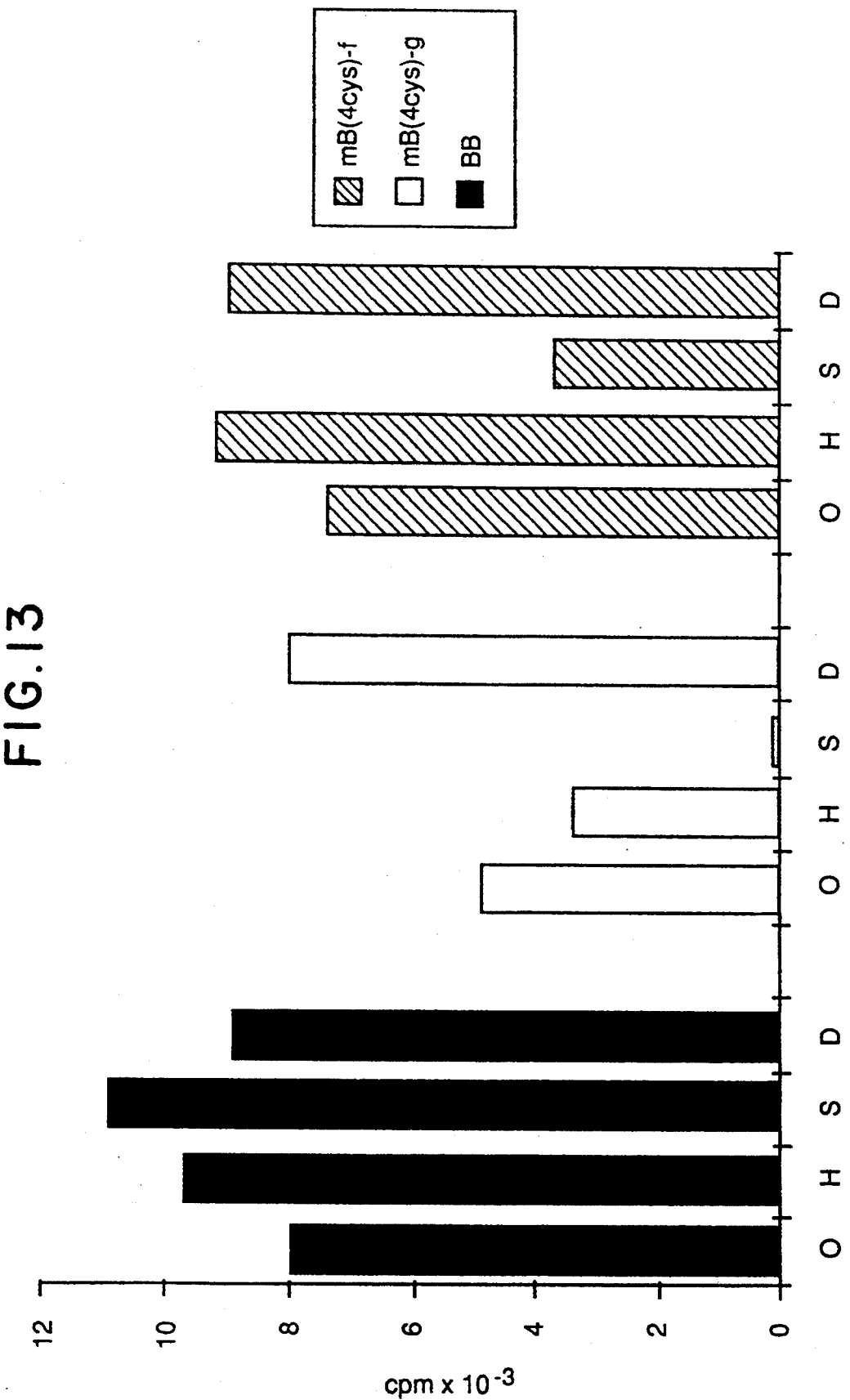
FIGS. 13 and 14 show the relative sensitivities of the monomeric mixed disulfide intermediate of PDGF $B_{109}$ [Ser43,Ser52,Ser53,Ser99] analog and the unblocked PDGF $B_{109}$ [$Ser^{43}$,$Ser^{52}$,$Ser^{53}$,$Ser^{99}$] analog, as compared with PDGF $B_{119}$ homodimer, when exposed to various agents.

Each protein was treated in one of three ways: (1) boiling for 10 minutes ("H"); (2) adjusted to 0.1% SDS ("S"); and incubated with 10 mM dithiothreitol (DTT) for 10 minutes at 37° C. ("D"). The mB(4cys)-g and mB(4cys)-f monomers were diluted to 5,000 ng/ml, with PDGF-BB being diluted to 50 ng/ml, prior to assay for mitogenic activity, as described in Example 3. The results are shown in FIG. 13, with the untreated sample being designated "∅". As FIG. 13 confirms, both monomeric forms showed the expected sensitivity to SDS, with the mixed disulfide intermediate mB(4cys)-g losing nearly all activity in the presence of SDS. The dimeric PDGF-BB form demonstrated no loss of activity upon exposure to SDS.

B. Effects of SDS and Strongly Reducing Conditions

Figure 14:
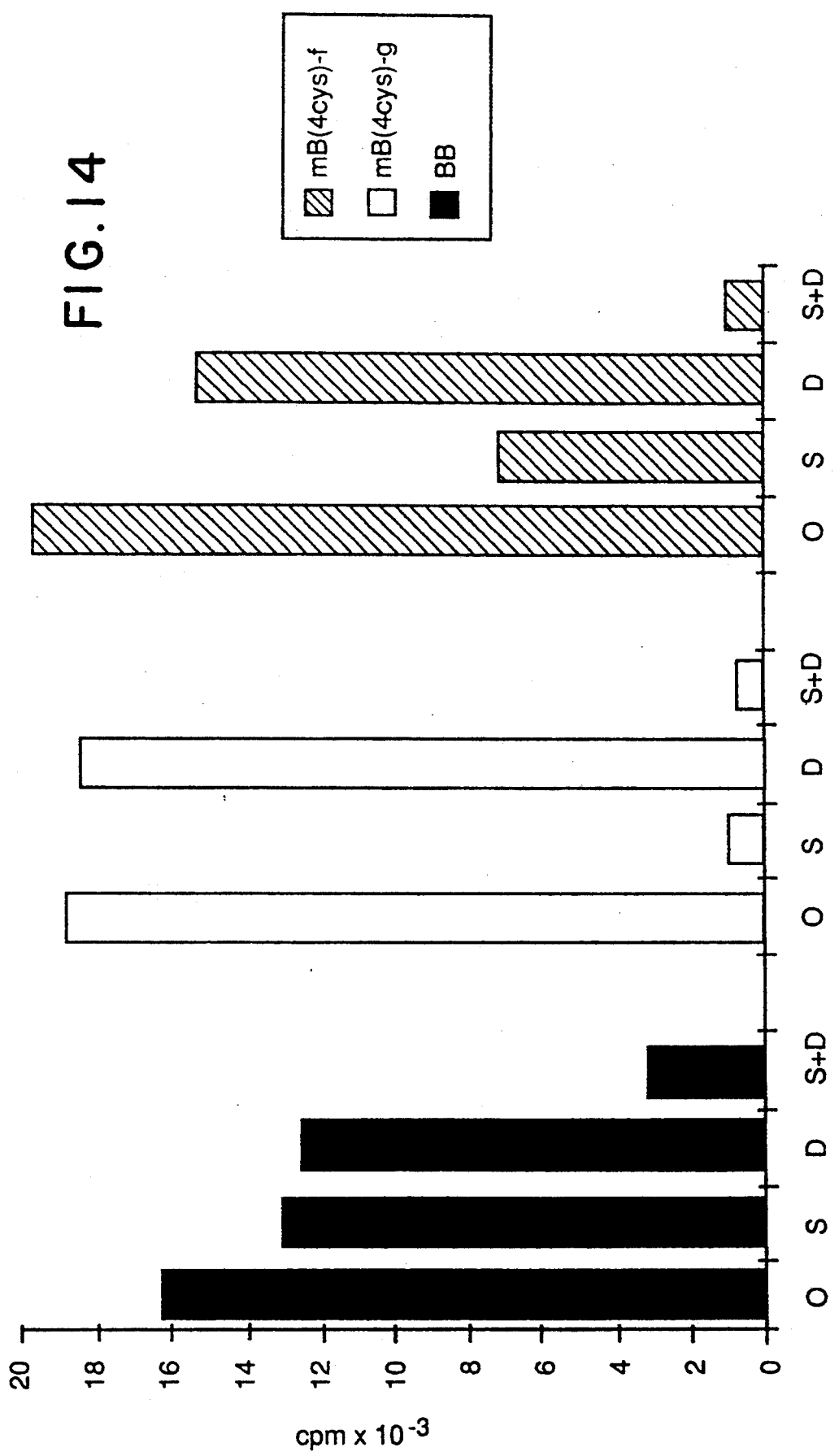

Each protein was treated in one of three ways: (1) adjusted to 0.1% SDS ("S"); (2) boiling in 10 mM DTT for 10 minutes ("D"); and (3) boiling in a combination of 0.1% SDS and 10 mM DTT for 10 minutes ("S+D"). The mB(4cys)-g and mB(4cys)-f monomers were diluted to 5,000 ng/ml, with PDGF-BB being diluted to 50 ng/ml, prior to assay for mitogenic activity, as described in Example 3. The results are shown in FIG. 14, with the untreated sample being designated "∅". The same results were obtained with respect to exposure to SDS as shown in FIG. 13 from the previous experiment. In addition, both monomeric forms showed significantly greater sensitivity to the combination of SDS and DTT that was observed for the dimeric PDGF-BB.

In summary, the differential properties of the activities of PDGF monomers and dimer described above demonstrate that the mitogenic activity of the monomers is not due to small amounts of dimer being present in the samples. First, no dimer is visible on SDS-PAGE analysis. Second, the monomers appear to exhibit a "superactivity" not observed with dimer. Finally, the mitogenic activity of monomers is sensitive to heat and SDS, whereas the mitogenic activity of dimer is not.

What is claimed is:

1. A mixed dimeric recombinant platelet-derived growth factor characterized in that one of the monomeric subunits of said mixed dimeric recombinant platelet-derived growth factor is PDGF B$_{109}$ and the other of said subunits is a different form of the B chain of platelet-derived growth factor.

2. A mixed dimeric recombinant platelet-derived growth factor characterized in that one of the monomeric subunits of said mixed dimeric recombinant platelet-derived growth factor is PDGF B$_{119}$ and the other of said subunits is a different form of the B chain of platelet-derived growth factor.

3. A mixed dimeric recombinant platelet-derived growth factor characterized in that one of the monomeric subunits of said mixed dimeric recombinant platelet-derived growth factor is PDGF B$_{109}$ and the other of said subunits is PDGF B$_{119}$.

* * * * *